United States Patent
Johnson et al.

(10) Patent No.: US 10,927,365 B2
(45) Date of Patent: Feb. 23, 2021

(54) MANIPULATING THE CIRCADIAN CLOCK TO INCREASE GENE EXPRESSION

(71) Applicant: Vanderbilt University, Nashville, TN (US)

(72) Inventors: Carl Hirschie Johnson, Nashville, TN (US); Philip D. Weyman, Cardiff, CA (US); Qing Xu, North Potomac, MD (US); Yao Xu, Nashville, TN (US)

(73) Assignee: VANDERBILT UNIVERSITY, Nashville, TN (US)

( * ) Notice: Subject to any disclaimer, the term of this patent is extended or adjusted under 35 U.S.C. 154(b) by 0 days.

(21) Appl. No.: 14/933,622

(22) Filed: Nov. 5, 2015

(65) Prior Publication Data

US 2016/0289646 A1    Oct. 6, 2016

Related U.S. Application Data

(60) Provisional application No. 62/076,040, filed on Nov. 6, 2014.

(51) Int. Cl.
| | | |
|---|---|---|
| *C12N 15/00* | (2006.01) | |
| *C12N 9/02* | (2006.01) | |
| *C07K 14/195* | (2006.01) | |
| *C12N 15/74* | (2006.01) | |
| *C12N 15/82* | (2006.01) | |
| *C07K 14/62* | (2006.01) | |

(52) U.S. Cl.
CPC .......... *C12N 15/00* (2013.01); *C07K 14/195* (2013.01); *C12N 9/0067* (2013.01); *C12N 15/74* (2013.01); *C12N 15/8222* (2013.01); *C12Y 112/00* (2013.01); *C07K 14/62* (2013.01)

(58) Field of Classification Search
None
See application file for complete search history.

(56) References Cited

U.S. PATENT DOCUMENTS

| 8,039,434 B2 * | 10/2011 | Mannen .................. C12P 21/02 |
| | | 424/245.1 |
| 9,074,006 B2 | 7/2015 | Himanen et al. |
| 2014/0186877 A1 | 7/2014 | Reppas et al. |

OTHER PUBLICATIONS

Thomas et al (1996, The Journal of Biological Chemistry 271 (19): 11141-11147).*
Kano-Murakami et al (1993, "A Rice Homeotic Gene, OSH1, Causes Unusual Phenotypes in Transgenic Tobacco". FEBS 334:365-368).*
Ishiura et al (1998, Science 281(5382): 1519-1523).*
Ishiura et al (1998, Science 281(5382): 1519-1523) (Year: 1998).*
Ishiura et al (1999, NCBI accession No. AB010691) (Year: 1999).*
Xu (2013 "Circadian Yin-Yang Regulation and Its Manipulation to Globally Reprogram Gene Expression", Current Biology 23(23): 2365-2374).*
Ishiura et al (1999, NCBI accession No. AB010691).*
Ishiura et al (1998, "Expression of a Gene Cluster kaiABC as a Circadian Feedback Process in Cyanobacteria", Science 281(5382): 1519-1523).*
Huang et al (2010, "Design and Characterization of Molecular Tools Fora Synthetic Biology Approach Towards Developing Cyanobacterial Biotechnology", Nucleic Acid Research 38(8): 2577-2593).*
Barak, Simon, et al. "All in good time: the *Arabidopsis* circadian clock." *Trends in plant science* 5.12 (2000): 517-522.
Ducat, Daniel C. et al. "Engineering cyanobacteria to generate high-value products." *Trends in biotechnology* 29.2 (2011): 95-103.
Elledge et al. "Genetic selection for genes encoding sequence-specific DNA-binding proteins." *Proceedings of the National Academy of Sciences* 86.10 (1989): 3689-3693.
Fritsch et al. "Structure, function and biosynthesis of O2-tolerant hydrogenases." *Nature Reviews Microbiology* 11.2 (2013): 106-114.
Gendron et al. "*Arabidopsis* Circadian Clock Protein, TOC1, Is a DNA-Binding Transcription Factor." *Proceedings of the National Academy of Sciences of the United States of America* 109.8 (2012): 3167-3172.
Gille, H et al. "The FIS Protein Binds and Bends the Origin of Chromosomal DNA Replication, oriC, of *Escherichia coli*." *Nucleic Acids Research* 19.15 (1991): 4167-4172.
Gutu et al. "Two Antagonistic Clock-Regulated Histidine Kinases Time the Activation of Circadian Gene Expression." *Molecular cell* 50.2 (2013): 288-294.
Ishiura et al. "Expression of a gene cluster kaiABC as a circadian feedback process in cyanobacteria." *Science* 281.5382 (1998): 1519-1523.
Ito, et al. "Cyanobacterial Daily Life with Kai-Based Circadian and Diurnal Genome-Wide Transcriptional Control in *Synechococcus elongatus*." *Proceedings of the National Academy of Sciences of the United States of America* 106.33 (2009): 14168-14173.
Iwasaki et al. "KaiA-Stimulated KaiC Phosphorylation in Circadian Timing Loops in Cyanobacteria." *Proceedings of the National Academy of Sciences of the United States of America* 99.24 (2002): 15788-15793.
Kindle et al. "Engineering the Chloroplast Genome: Techniques and Capabilities for Chloroplast Transformation in Chlamydomonas Reinhardtii." *Proceedings of the National Academy of Sciences of the United States of America* 88.5 (1991): 1721-1725.
Kondo et al. "Circadian Rhythms in Prokaryotes: Luciferase as a Reporter of Circadian Gene Expression in Cyanobacteria." *Proceedings of the National Academy of Sciences of the United States of America* 90.12 (1993): 5672-5676.
Kutsuna et al. "The Circadian Clock-Related Gene pex Regulates a Negative cis Element in the kaiA Promoter Region." *Journal of Bacteriology* 189.21 (2007): 7690-7696.

(Continued)

*Primary Examiner* — Stuart F Baum
(74) *Attorney, Agent, or Firm* — Parker Highlander PLLC

(57) ABSTRACT

A method of increasing gene expression by manipulating the circadian clock is described that includes transforming a photosynthetic organism to include an expression control sequence that modulates the expression of a clock gene to increase expression of a target gene. Photosynthetic organism having a modified circadian cycle reflecting this method are also described.

13 Claims, 14 Drawing Sheets

Specification includes a Sequence Listing.

(56) References Cited

OTHER PUBLICATIONS

Liu, Tiffany, et al. "Direct regulation of abiotic responses by the *Arabidopsis* circadian clock component PRR7." *The plant journal* 76.1 (2013): 101-114.
Liu, Yi, et al. "Circadian orchestration of gene expression in cyanobacteria." *Genes & development* 9.12 (1995): 1469-1478.
McClung, C. Robertson. "Plant Circadian Rhythms." *The Plant Cell* 18.4 (2006): 792-803.
Min, et al. "Phase determination of circadian gene expression in Synechococcus elongatus PCC 7942." *Journal of biological rhythms* 19.2 (2004): 103-112.
Mori et al. "Independence of Circadian Timing from Cell Division in Cyanobacteria." *Journal of Bacteriology* 183.8 (2001): 2439-2444.
Nagel et al. "Genome-wide identification of CCA1 targets uncovers an expanded clock network in *Arabidopsis*." *Proceedings of the National Academy of Sciences* 112.34 (2015): E4802-E4810.
Nakahira et al. "Global Gene Repression by KaiC as a Master Process of Prokaryotic Circadian System." *Proceedings of the National Academy of Sciences of the United States of America* 101.3 (2004): 881-885.
Nakamichi et al. "Transcript profiling of an *Arabidopsis* Pseudo Response Regulator arrhythmic triple mutant reveals a role for the circadian clock in cold stress response." *Plant and Cell Physiology* 50.3 (2009): 447-462.
Okamoto et al. "A compact multi-channel apparatus for automated real-time monitoring of bioluminescence." *Journal of biochemical and biophysical methods* 70.4 (2007): 535-538.
Qin et al. "Intermolecular Associations Determine the Dynamics of the Circadian KaiABC Oscillator." *Proceedings of the National Academy of Sciences of the United States of America* 107.33 (2010): 14805-14810.
Radakovits et al. "Genetic Engineering of Algae for Enhanced Biofuel Production." *Eukaryotic Cell* 9.4 (2010): 486-501.
Taniguchi et al. "Three Major Output Pathways from the KaiABC-Based Oscillator Cooperate to Generate Robust Circadian kaiBC Expression in Cyanobacteria." *Proceedings of the National Academy of Sciences of the United States of America* 107.7 (2010): 3263-3268.
Tomita et al. "No transcription-translation feedback in circadian rhythm of KaiC phosphorylation." *Science* 307.5707 (2005): 251-254.
Vijayan et al. "Oscillations in Supercoiling Drive Circadian Gene Expression in Cyanobacteria." *Proceedings of the National Academy of Sciences of the United States of America* 106.52 (2009): 22564-22568.
Wang et al. "Application of Synthetic Biology in Cyanobacteria and Algae." *Frontiers in Microbiology* 3 (2012): 344.
Weyman et al. "Heterologous Expression of *Alteromonas macleodii* and *Thiocapsa roseopersicina* [NiFe] Hydrogenases in *Synechococcus elongatus*." Ed. Francisco Rodriguez-Valera. *PLoS ONE* 6.5 (2011): e20126.
Woelfle et al. "Circadian Rhythms of Superhelical Status of DNA in Cyanobacteria." *Proceedings of the National Academy of Sciences of the United States of America* 104.47 (2007): 18819-18824.
Xu, Yao et al. "Cyanobacterial Circadian Clockwork: Roles of KaiA, KaiB and the kaiBC Promoter in Regulating KaiC." *The EMBO Journal* 22.9 (2003): 2117-2126.
Atsumi, Shota, Wendy Higashide, and James C. Liao. "Direct photosynthetic recycling of carbon dioxide to isobutyraldehyde." *Nature Biotechnology* 27.12 (2009): 1177.
Gordon, Gina C., et al. "CRISPR interference as a titratable, trans-acting regulatory tool for metabolic engineering in the cyanobacterium Synechococcus sp. strain PCC 7002." *Metabolic Engineering* 38 (2016): 170-179.
Higo, Akiyosbi, et al. "Designing synthetic flexible gene regulation networks using RNA devices in cyanobacteria." *ACS Synthetic Biology* 6.1 (2016): 55-61.
Huang, Hsin-Ho, et al. "Design and characterization of molecular tools for a synthetic biology approach towards developing cyanobacterial biotechnology." *Nucleic Acids Research* 38.8 (2010): 2577-2593.
Jazmin, Lara J., et al. "Isotopically nonstationary 13C flux analysis of cyanobacterial isobutyraldehyde production." *Metabolic Engineering* 42 (2017): 9-18.
Niederholtmeyer, Henrike, et al. "Engineering cyanobacteria to synthesize and export hydrophilic products." *Appl. Environ. Microbiol.* 76.11 (2010): 3462-3466.
Ungerer, Justin, et al. "Sustained photosynthetic conversion of CO 2 to ethylene in recombinant cyanobacterium Synechocystis 6803," *Energy & Environmental Science* 5.10 (2012): 8998-9006.
Wolk, C. Peter, et al. "Amplified expression of a transcriptional pattern formed during development of Anabaena." *Molecular Microbiology* 7.3 (1993): 441-445.
Xiong, Wei, et al. "The plasticity of cyanobacterial metabolism supports direct CO 2 conversion to ethylene." *Nature Plants* 1.5 (2015): 15053.
Xu, Yao, et al. "Circadian yin-yang regulation and its manipulation to globally reprogram gene expression." *Current Biology* 23.23 (2013): 2365-2374.
Yao, Lun, et al. "Multiple gene repression in cyanobacteria using CRISPRi." *ACS Synthetic Biology* 5.3 (2015): 207-212.

\* cited by examiner

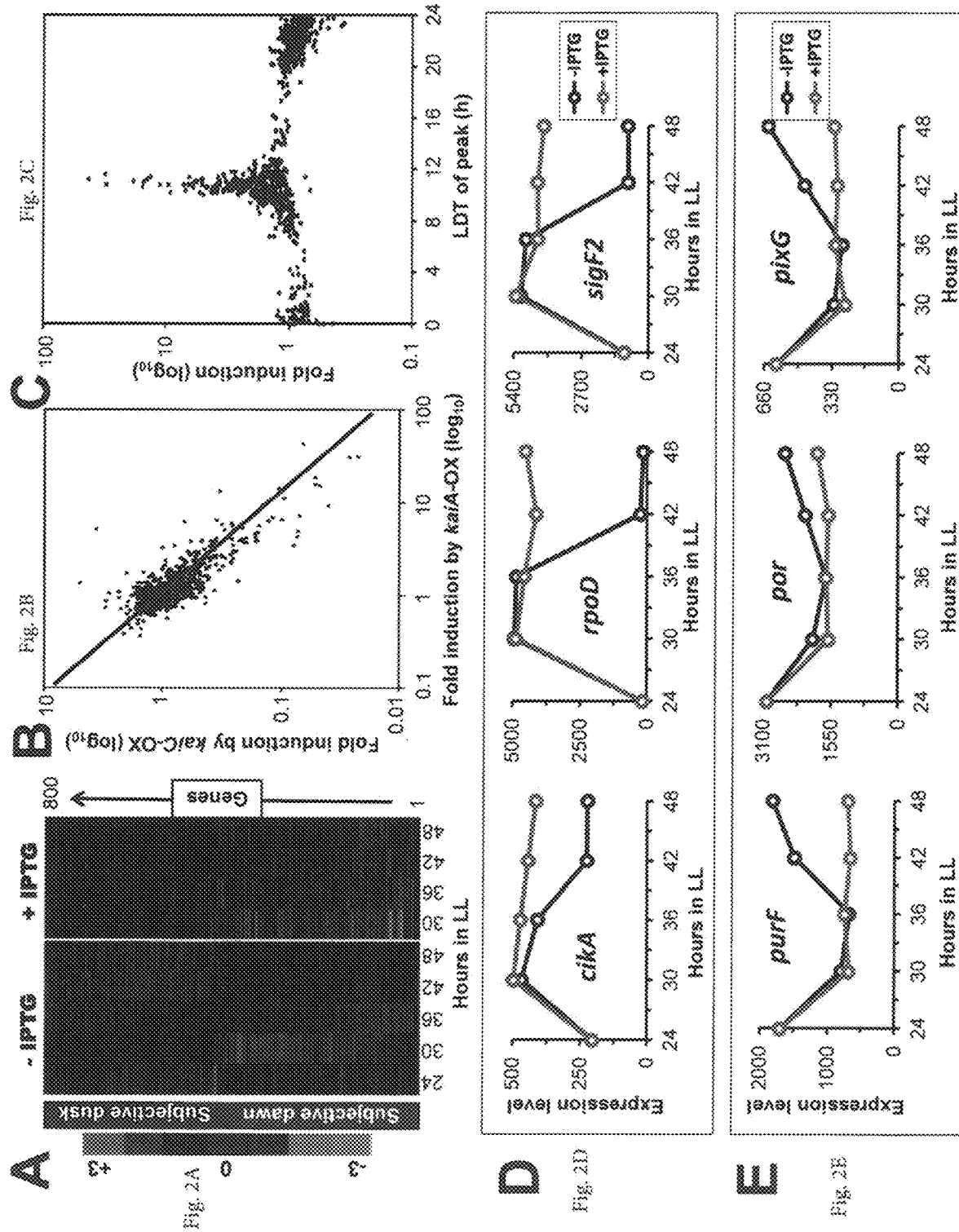

Fig. 3A
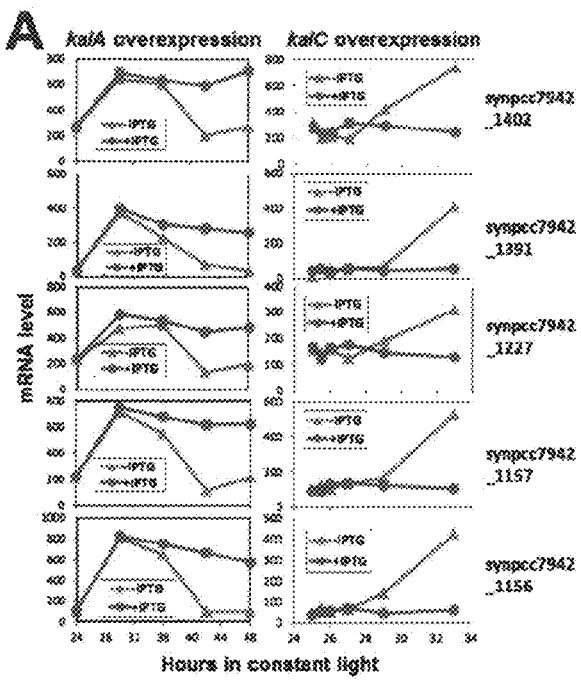
Fig. 3B
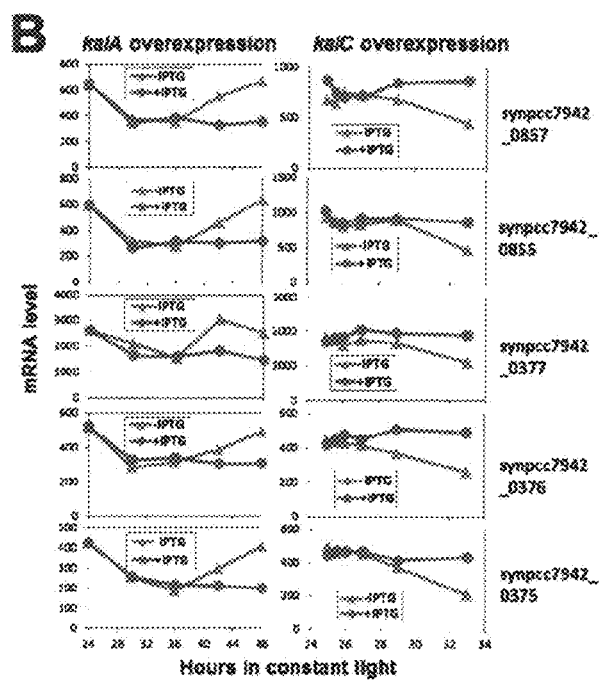
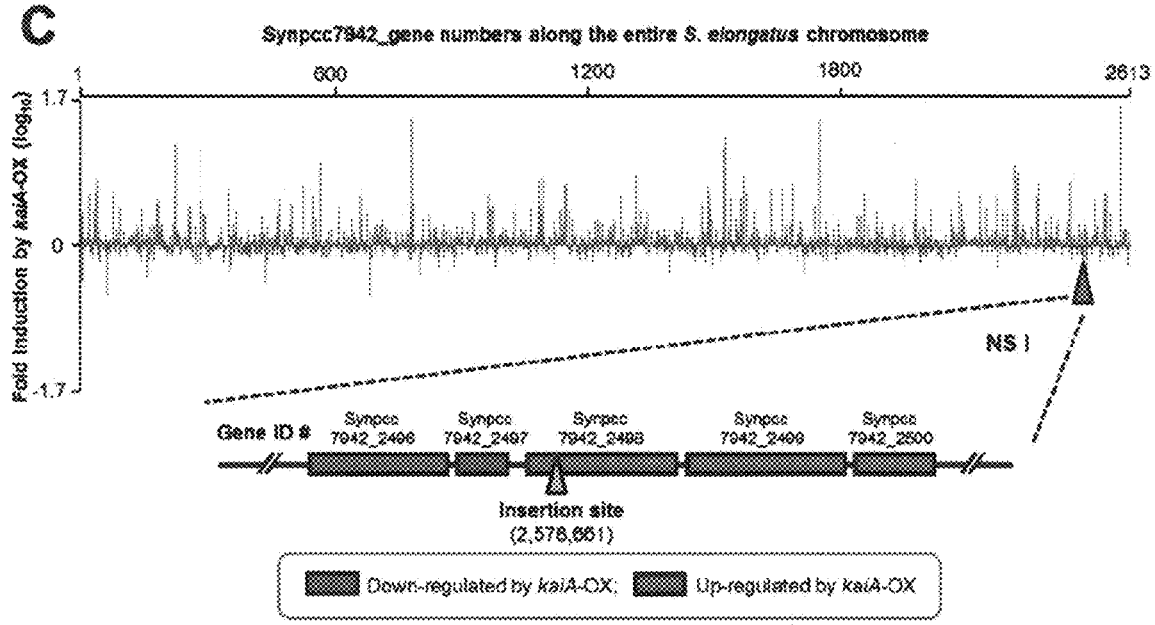
Fig. 3C

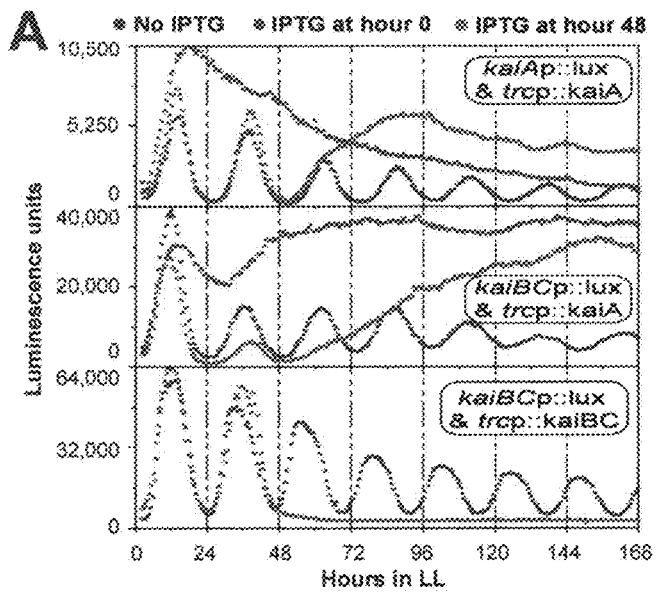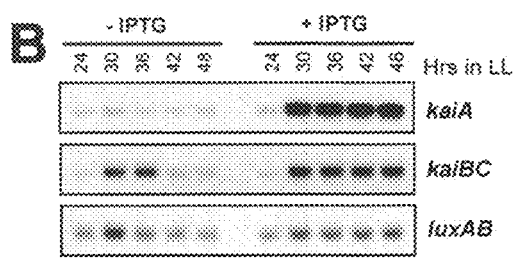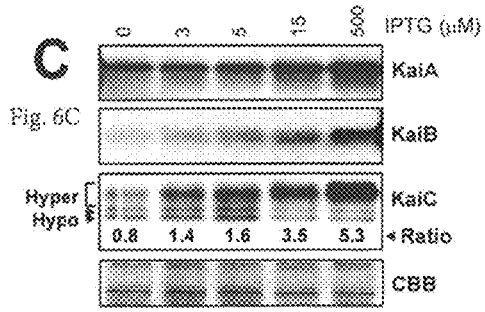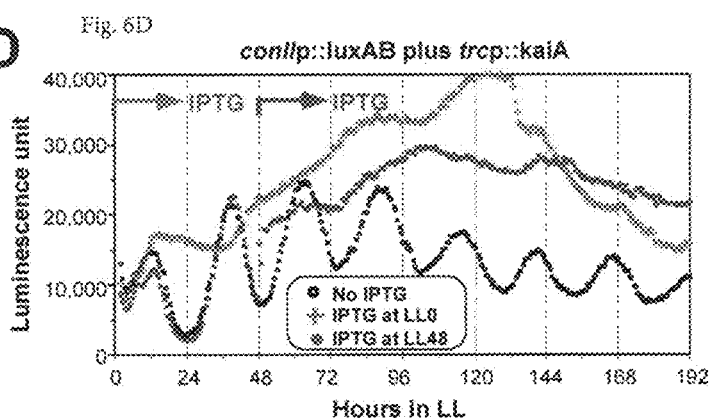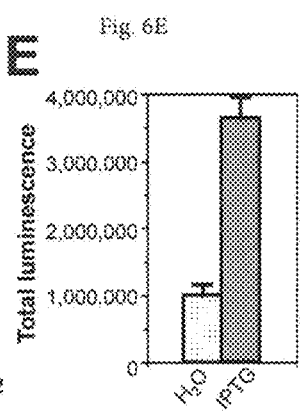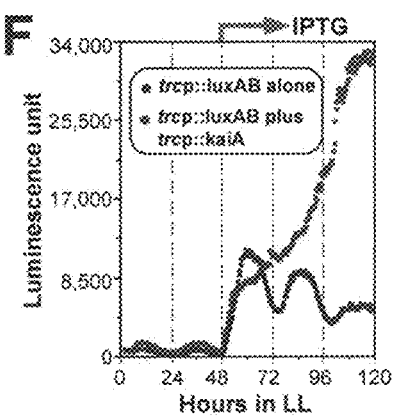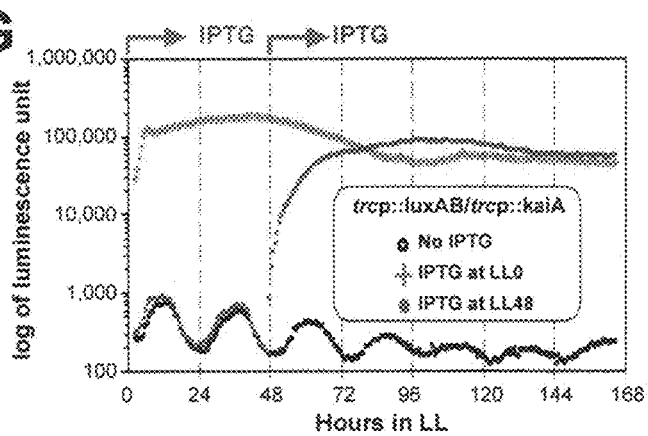

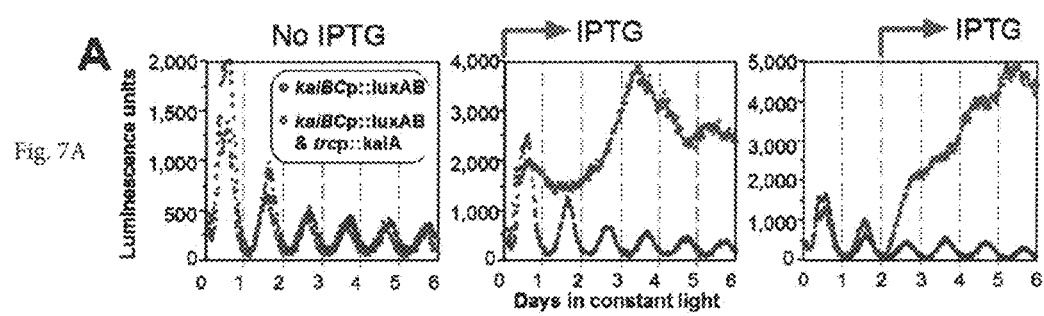
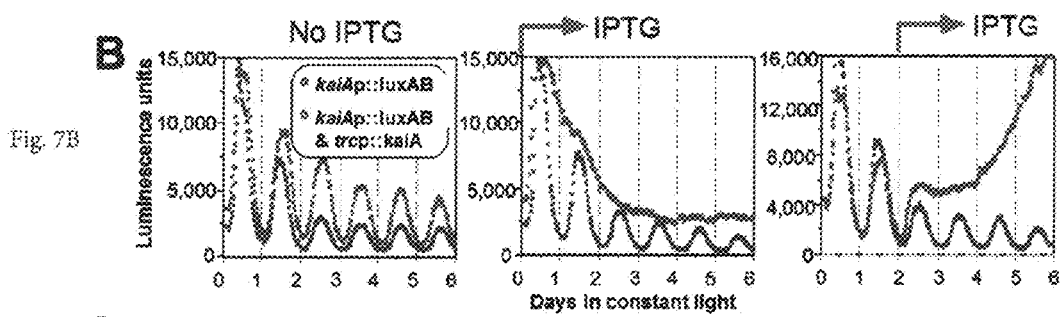
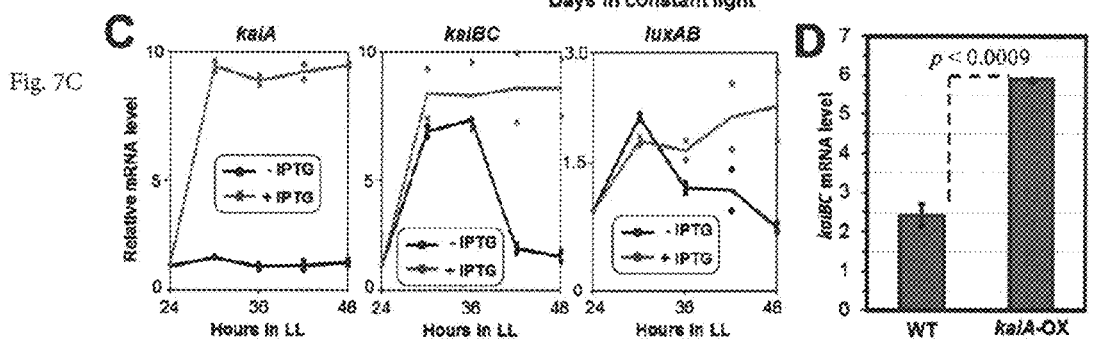
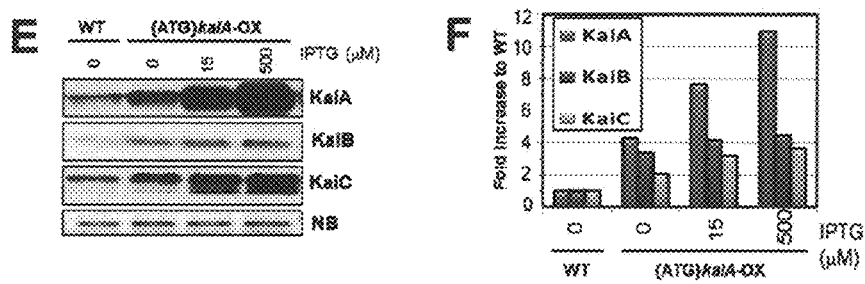
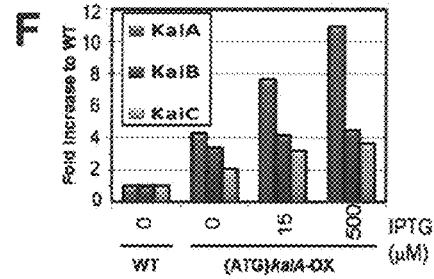
Fig. 7A
Fig. 7B
Fig. 7C
Fig. 7D
Fig. 7E
Fig. 7F

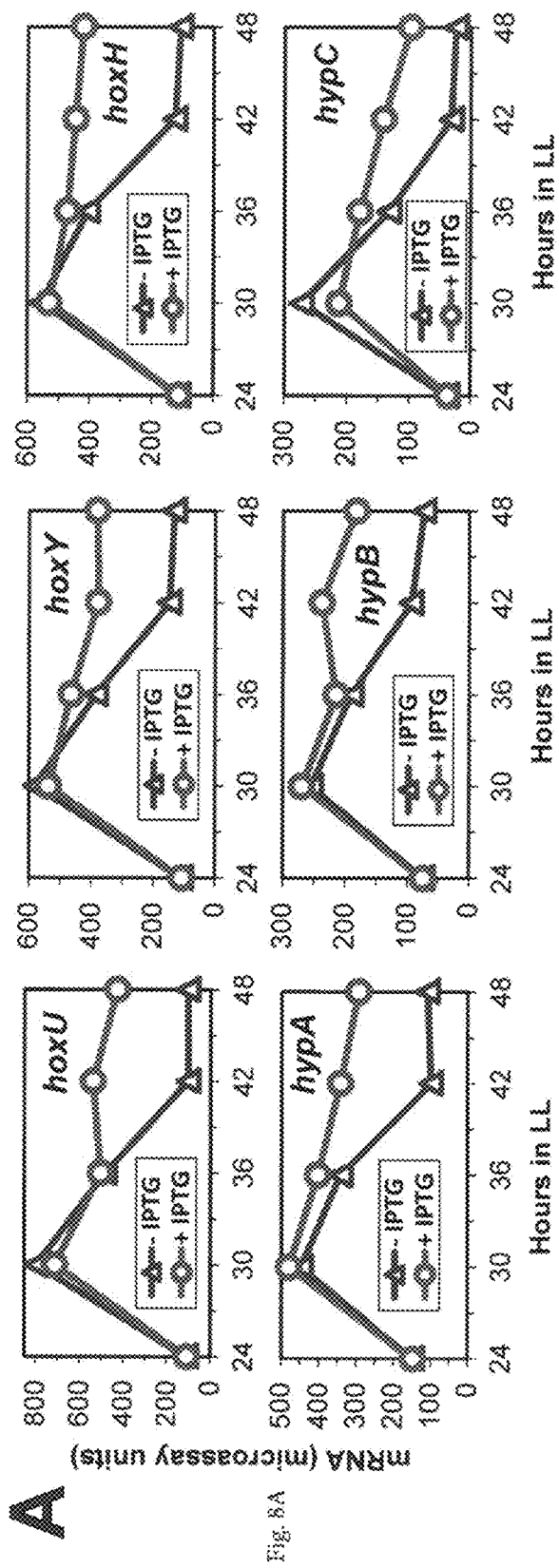
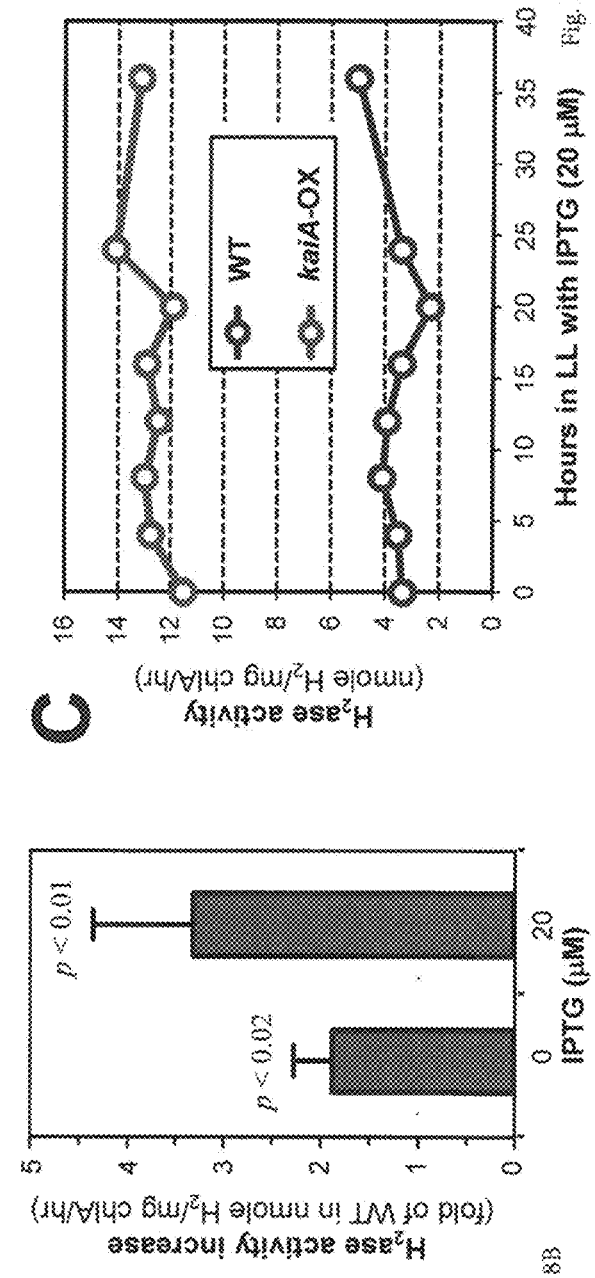
Fig. 8A
Fig. 8B
Fig. 8C

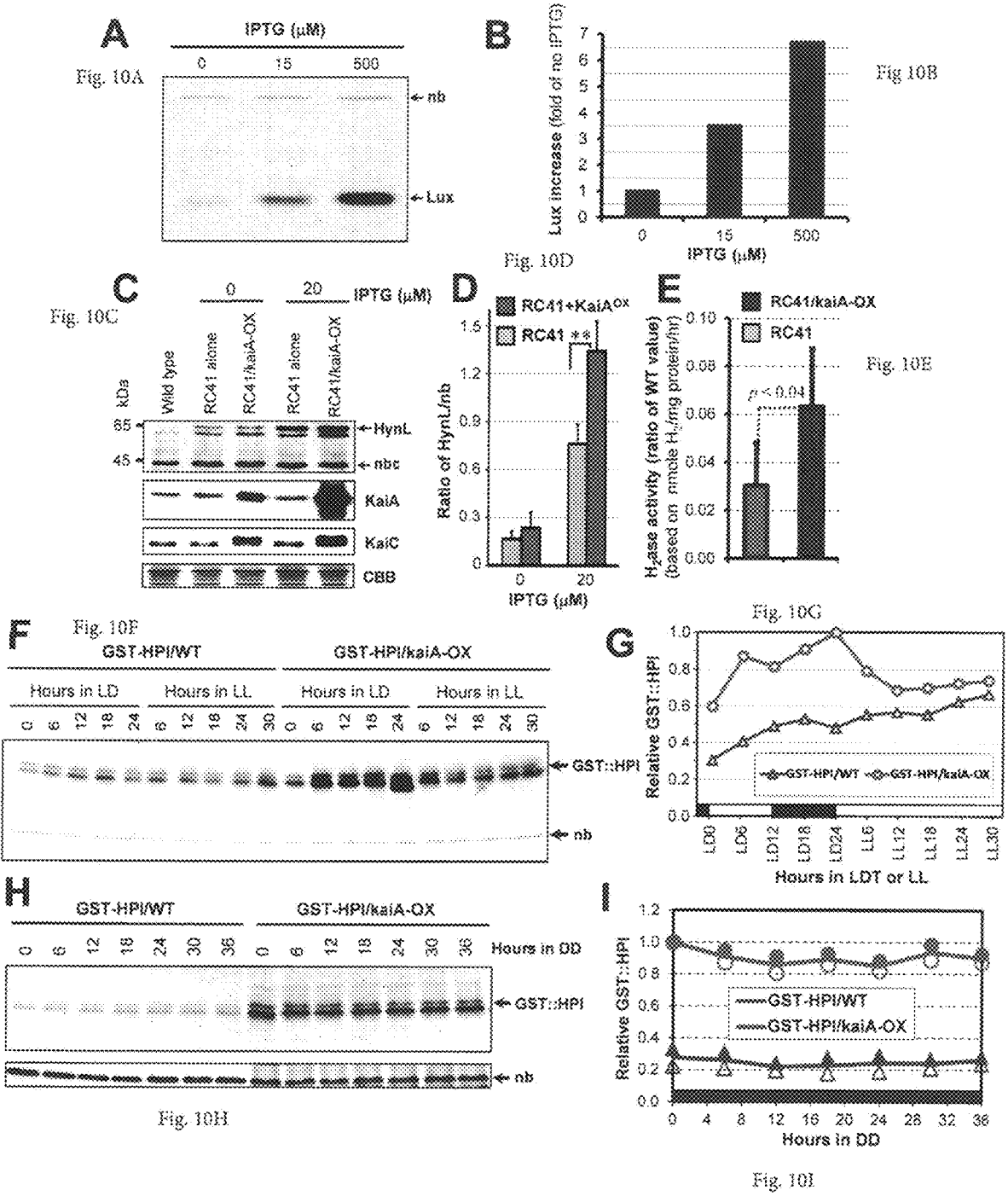

Fig. 11A
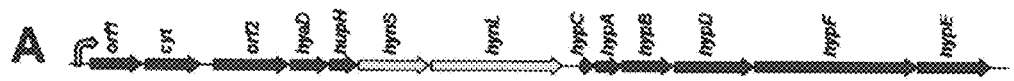
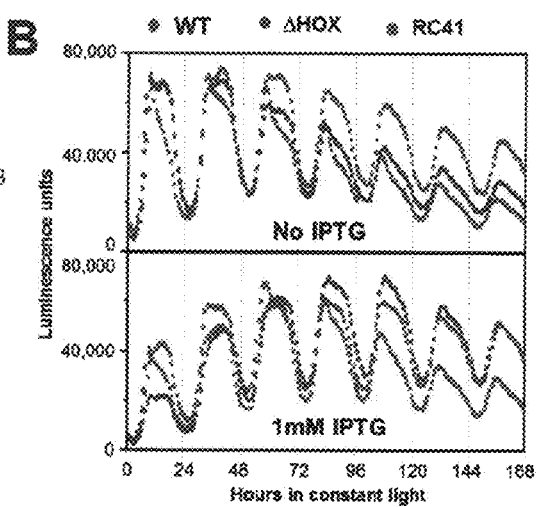
Fig. 11B
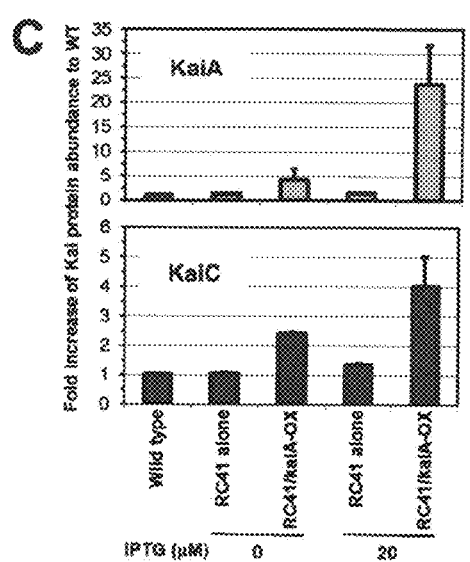
Fig. 11C
Fig. 11D
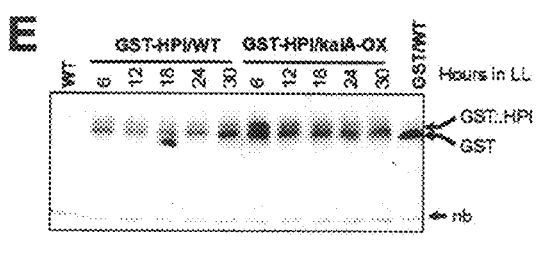
Fig. 11E
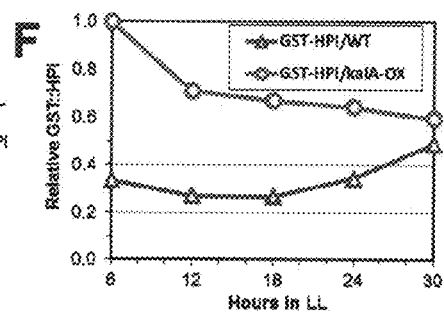
Fig. 11F

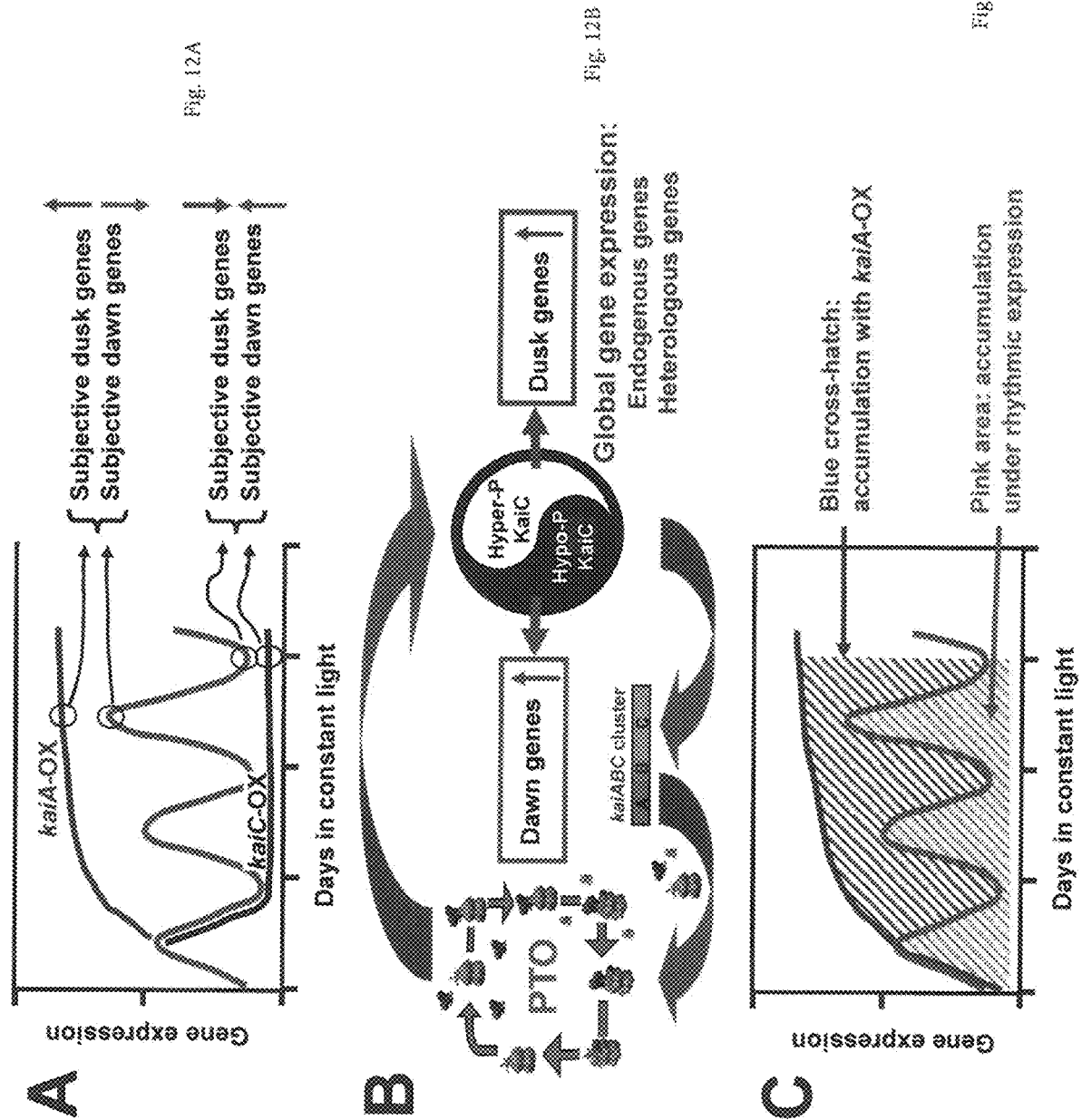

MANIPULATING THE CIRCADIAN CLOCK TO INCREASE GENE EXPRESSION

CROSS-REFERENCE TO RELATED APPLICATIONS

This application claims priority to U.S. Provisional Patent Application Ser. No. 62/076,040, filed Nov. 6, 2014, which is incorporated herein by reference.

STATEMENT REGARDING FEDERALLY SPONSORED RESEARCH

The present invention was supported by grants from the National Institute of General Medical Sciences (NIGMS R01 GM067152 and R01 GM088595) and the U.S. Department of Energy (DE-FG36-05GO15027). The Government has certain rights in this invention.

SEQUENCE LISTING

The instant application contains a Sequence Listing which has been submitted in ASCII format via EFS-Web and is hereby incorporated by reference in its entirety. Said ASCII copy, created on Nov. 4, 2015, is named Circadian Regulation_ST25 and is 30.2 kilobytes in size.

BACKGROUND

Circadian rhythms are circa-24 h oscillations in biological processes that are controlled by an endogenous biochemical pacemaker to provide a temporal program that allows organisms to optimally adapt to the daily transformation of environmental conditions. This "biological clock" rhythmically orchestrates intracellular activities that range from gene expression, metabolism, cell division, to development and behavior. In eukaryotes, approximately 10% of the genome is regulated by the daily clock in any given tissue. In the photoautotrophic cyanobacterium *Synechococcus elongatus* PCC 7942, virtually all gene expression is controlled at the level of promoter activity by the circadian clock (Liu et al., Genes Dev. 9, 1469-1478 (1995)), and 35-70% of steady-state transcript abundances oscillate. Vijayan et al., Proc. Natl. Acad. Sci. USA 106, 22564-22568 (2009). The entire chromosome even undergoes daily cycles of topological change and compaction that are related to this genome-wide transcriptional control.

The KaiA, KaiB, and KaiC proteins form the central clockwork in cyanobacteria, and the status of KaiC phosphorylation plays a key role in the central clock mechanism as well as global regulation of output gene expression. Gutu, A., and O'Shea, E. K., Mol. Cell 50, 288-294 (2013). KaiC is both an autokinase and an autophosphatase, but KaiA promotes phosphorylation of KaiC (Iwasaki et al., Proc. Natl. Acad. Sci. USA 99, 15788-15793 (2002)) while KaiB combines with KaiA and KaiC to form a complex that promotes KaiC dephosphorylation. Qin et al., Proc. Natl. Acad. Sci. USA. 107, 14805-14810 (2010). There are multiple pathways that link the central KaiABC post-translational oscillator (PTO) to its transcriptional outputs that include the proteins SasA, CikA, LabA, RpaA, and RpaB. In particular, RpaA appears to be a major output node that is regulated by KaiABC through independent SasA/CikA/LabA pathways. Taniguchi et al., Proc. Natl. Acad. Sci. USA 107, 3263-3268 (2010). The global gene expression patterns in *S. elongatus* are primarily organized into two groups that are phased 180° apart. Liu et al., Genes Dev. 9, 1469-1478 (1995). The "Class I" or "subjective dusk" genes activate at dawn and rise throughout the day to a peak expression at dusk, while the "Class II" or "subjective dawn" genes turn on in the subjective night and peak at dawn. The Class I (subjective dusk) genes are the predominant group. It has been reported that overexpression of kaiC represses the rhythmic components of all genes in the genome. Nakahira et al., Proc. Natl. Acad. Sci. USA 101, 881-885 (2004). However, a more recent microarray analysis concluded that kaiC overexpression represses the predominant Class I (dusk) genes, while up-regulating Class II (dawn) genes. Ito et al., Proc. Natl. Acad. Sci. USA 106, 14168-14173 (2009).

Insights into the regulation of gene expression in cyanobacteria are important for understanding the basic biology of circadian control, but also have potential applications. Because they derive their energy from the sun and are genetically malleable, photoautotrophic cyanobacteria are attractive bioreactors for synthesizing biofuels and other bioproducts. Ducat et al., Trends in Biotech. 29, 95-103 (2011). In particular, *S. elongatus* has become one of the preferred platforms for development of this biotechnology. However, despite the appeal of directing photosynthetic carbon fixation towards the production of useful molecules in cyanobacterial hosts, the efficiency of heterologous expression achieved by cyanobacteria is currently too low for industrial application. Furthermore, few tools are available to reprogram metabolic flux in photosynthetic microbes along pathways towards the synthesis of useful bioproducts or their precursors. Wang et al., Front Microbiol. 3, 344 (2012). Accordingly, there remains a need for methods and organisms in which the circadian clock is used to increase gene expression.

SUMMARY OF THE INVENTION

Due to the pervasive circadian control of promoter activities in cyanobacteria, experimental modulation of clock genes could be exploited to tune gene expression to operate maximally under constant-light conditions or to resonate in harmony with periodic light-dark cycling. In this study, the inventors examined the phased expression patterns and find that kaiA-vs. kaiC-overexpression (kaiA-OX vs. kaiC-OX) exhibit opposing actions over promoters such that the genome-wide patterns of both dusk (Class I) and dawn (Class II) genes can be explained. They refer to the opposing actions of kaiA-OX vs. kaiC-OX as a "Yin-Yang" interdependency, based on the Taoist concept of balancing forces that complementarily interact to promote harmony. This basic information was used to reprogram circadian clock-controlled circuits to switch from cycling to constitutive gene expression as well as manipulating the expression of the kaiA gene to enhance expression of endogenous and foreign genes. As proof of principle, this strategy was applied towards optimizing the expression of endogenous and foreign [NiFe] hydrogenases for biohydrogen production and expression of foreign genes such as luciferase and human proinsulin, which serves as a test case for production of pharmaceuticals in cyanobacteria.

In one aspect, the invention provides a method of increasing gene expression by manipulating the circadian clock, comprising transforming a photosynthetic organism to include an expression control sequence that modulates the expression of a clock gene to increase expression of a target gene. In some embodiments, the photosynthetic organism is a plant, while in other embodiments the photosynthetic organism is a photoautotrophic or photoheterotrophic bacteria, such as a cyanobacteria.

Expression of the clock gene can be modulated in a variety of ways. In some embodiments, the clock gene is selected from the group consisting of KaiA, KaiB, and KaiC. In another embodiment, the clock gene is KaiA or KaiC and the clock gene is overexpressed. In further embodiments, the expression control sequence includes a promoter that is operably linked to the clock gene. In some embodiments, the expression of the target gene is operably linked to expression of the clock gene, while in other embodiments modulating expression of a clock gene suppresses the circadian rhythm of the photosynthetic organism. In a yet further embodiment, modulation of the clock gene is decreased expression of the clock gene, and the expression control sequence comprises a knockout mutation.

The invention can be used to increase the expression of a variety of different target genes. In some embodiments, the target gene is a biofuel product or biofuel precursor expressing gene. In other embodiments, the photosynthetic organism is a transgenic photosynthetic organism, and the target gene is a heterologous gene. Examples of heterologous genes include hydrogenase expressing genes and pro-insulin expressing genes.

Another aspect of the invention provides a photosynthetic organism having a modified circadian cycle, comprising a photosynthetic organism that has been transformed to include an expression control sequence that modulates the expression of a clock gene to increase expression of a target gene. In some embodiments, the photosynthetic organism is a plant, while in other embodiments the photosynthetic organism is a photoautotrophic or photoheterotrophic bacteria, such as a cyanobacteria. The photosynethetic organisms can be modified to modulate clock gene expression using any of the methods described herein, to increase the expression of any of the target genes described herein.

BRIEF DESCRIPTION OF THE FIGURES

The present invention may be more readily understood by reference to the following drawings wherein:

FIGS. 2A-2E provide graphs and images showing the microarray profiles of cycling genes in the kaiA-overexpressing (kaiA-OX) strain (A) Expression profiles of 800 cycling genes in the kaiA-OX strain in LL with or without 1 mM IPTG. These genes were sorted by peak time expressed by wild-type strains. The colors represent normalized data arranged in descending order, representing expression levels from high to low. The average and S.D. over one cycle is 0.0 and 1.0, respectively. (B) Correlation of the level of induction for ~800 circadian cycling genes. The expression level of each clock-controlled gene in Ptrc::kaiA cells in the presence of IPTG at LL48 was compared with that in the absence of IPTG at LL48. The abscissa indicates the fold induction by kaiA overexpression at LL48. The ordinate indicates the fold induction by kaiC overexpression at LL33 for the same genes (regression line is $R^2=0.683$). (C) Induction of KaiA up-regulates and down-regulates subjective dusk and dawn genes, respectively. The expression level of each clock-controlled gene in trcp::kaiA cells in the presence of IPTG at LL48 was compared with that in the absence of IPTG at LL48. The ordinate shows the amount of induction of each gene by kaiA-OX, while the abscissa indicates the peak time of each of the 800 cycling genes in Circadian Time, (CT0/24=dawn, CT12=dusk). (D) and (E) Temporal expression profiles of representative kaiA-enhanced subjective dusk genes (D) and kaiA-repressed subjective down genes (E) from microarray analysis. Expression profiles of genes in the kaiA-OX strain are shown with or without 1 mM IPTG. The number in the ordinate indicates relative expression level.

FIGS. 3A-3C provides graphs showing the opposing responses of some representative genes' expression to kaiA vs. kaiC overexpression and genome-wide expression patterns regulated by kaiA-OX. (A & B) Microarray data on mRNA abundances in response to kaiA vs. kaiC overexpression were compared from continuous cultures of the kaiA-overexpressing strain (this work) and a previously reported kaiC-overexpressing strain (Xu et al., EMBO J. 19, 3349-3357 (2000)) in the presence or absence of IPTG applied at LL24 (kaiA-OX strain) or LL25 (kaiC-OX strain). Five examples of genes upregulated by kaiA overexpression but downregulated by kaiC overexpression are shown in panel (A), and five examples of genes down-regulated by kaiA overexpression but up-regulated by kaiC overexpression in panel (B). The genes are identified on the right side of each panel. (C) Spatial distribution of kaiA-OX-regulated gene expression in the genome. Shown is the ratio of the expression level of each gene in trcp::kaiA cells in the presence of IPTG to that in the absence of IPTG at hour 48 in LL. Each ratio was arranged in ascending order of Synpcc7942 gene number. Lower panel shows flanking regions to Neutral Site I (NS I) and their responses to kaiA-OX.

FIGS. 6A-6G provide graphs showing that KaiA enhances expression of the central clock genes and E. coli promoters. (A) Constant kaiA-OX activates expression of the central clock genes and attenuates rhythmicity. Luminescence profiles were measured in a kaiA reporter (kaiAp::luxAB in NS I, i.e. kaiAp::lux) or kaiBC reporter (kaiBCp::luxAB in NS I, i.e. kaiBCp::lux) co-expressing trcp::kaiA with or without IPTG. A final concentration of 1 mM IPTG was applied either at LL0 (hour 0) or LL48 (hour 48) of constant light (LL) exposure. As a comparison with KaiC-induced repression, the kaiBC reporter strain (kaiBCp::luxAB, i.e. kaiBCp::lux) co-expressing trcp::kaiBC was performed in parallel for IPTG application at LL48. (B) Northern blot assays for mRNA expression of kaiA, kaiBC, and luxAB in the kaiA-overexpressing reporter strain with or without IPTG in LL. (C) KaiA-OX enhances the abundance of KaiB and KaiC proteins and hyper-phosphorylates KaiC. Cultures were collected at Circadian Time 04 (CT04) in LL in presence of different concentrations of IPTG. Ratios of hyper-P KaiC to hypo-P KaiC are shown numerically below the KaiC blots. The bottom row shows equivalent loading by Coomassie Brilliant Blue (CBB) staining. (D) kaiA-OX promotes constant high expression of the luxAB luminescence driven by the E. coli conII promoter in the cyanobacterial reporter strain (conIIp::luxAB) co-expressing trcp::kaiA in the absence or presence of IPTG (i.e. $H_2O$ [No IPTG] or 1 mM IPTG at LL0 or LL48). (E) Overall effect of kaiA overexpression on conII promoter activity. Total luminescence units in LL for 7 days were collected from cultures of uniform cell density (30 μl at $OD_{750}$=0.3) placed on agar medium from the conIIp::luxAB strain co-expressing trcp::kaiA in the absence ($H_2O$) or presence of 1 mM inducer (IPTG). (mean+/–S.D. for triplicates) (F) KaiA expression potentiates induction by the IPTG-derepressible heterologous trc promoter. Luminescence expression profiles were compared between a strain harboring the trcp::luxAB reporter alone and a strain co-expressing both the trcp::luxAB reporter and trcp::kaiA in the absence or presence of 1 mM IPTG added at LL48. (G) Co-induction of the reporter activities by the IPTG and KaiA in the trcp::luxAB reporter strain co-expressing trcp::kaiA in the absence (No IPTG) or in the presence of 1 mM IPTG started at LL0 or LL48. Note the $log_{10}$ scale for the ordinate.

FIGS. 7A-7F provides graphs showing that overexpression of kaiA enhances expression of the central kai clock genes. (A & B) Comparison of luminescence expression profiles between reporter strains for two different kai promoters (kaiBCp::luxAB or kaiAp::luxAB) alone and strains with the same reporters co-expressing trcp::kaiA in the absence or presence of 1 mM IPTG in LL applied at day 0 or day 2. (A) kaiBCp::luxAB reporter alone vs. kaiBCp::luxAB strain co-expressing trcp::kaiA. (B) kaiAp::luxAB reporter alone vs. kaiAp::luxAB strain co-expressing trcp::kaiA. (C) Densitometry of the Northern blotting data shown in FIG. 6B. Results from two separate experiments are shown (one of which is depicted in FIG. 6B) and the lines connect the averages of these replicates. (D) qRT-PCR analysis of kaiBC mRNA activation by kaiA overexpression. Cells from wild-type (WT) or kaiA-overexpressing (kaiA-OX) strains were released to LL after 2 two cycles of 12 h LD. At LL24, 1 mM IPTG was added and cells were collected at LL34 for qRT-PCR assays for kaiBC mRNA. (E) Hyper-induction of {ATG}KaiA protein by IPTG and its enhancement of KaiB and KaiC protein abundances. The cultures from {ATG}kaiA-OX strain or wild-type strain (WT) were collected at CT12 in LL in presence of different concentrations of IPTG. Equal loadings were confirmed by the non-specific bands (NB) to KaiB. At CT12, KaiC is already mostly hyper-phosphorylated, and induction of {ATG}kaiA increases KaiC abundance while maintaining its hyperphosphorylation status. Note that the {ATG}kaiA overexpression construct with an ATG start codon is slightly "leaky," and even at 0 μM IPTG, there is some extra expression of KaiA that increases KaiB and hyper-P KaiC levels above the WT control. (F) Densitometry of the immunoblot data shown in panel E.

FIGS. 8A-8C provide graphs showing that KaiA promotes expression and activity of endogenous Hox hydrogenase ($H_2$ase). (A) kaiA-enhanced mRNA microarray profiles of all $H_2$ase subunits and $H_2$ase maturation genes (as denoted) in the kaiA-overexpressing strain with or without IPTG. (B) Hydrogenase activity increases in the {ATG}kaiA-OX strain relative to the wild-type (WT) strain in the absence or presence of IPTG induction. Data are represented as mean+/–SD from three independent experiments and analyzed with t-test. Note that the {ATG}kaiA overexpression construct is slightly "leaky", and even at 0 μM IPTG, there is some extra expression of KaiA above that in WT. (C) KaiA causes constantly high levels of hydrogenase activities under continuous light conditions. Following a 12 h of dark pulse, the endogenous hydrogenase activities were measured from samples of the WT and {ATG}kaiA-OX strains at the indicated times in LL.

FIGS. 10A-10I provide graphs and images showing that KaiA enhances expression and accumulation of foreign genes and proteins. (A) Accumulation of Vibrio harveyi luciferase (Lux) was enhanced by induction of kaiA with or without IPTG (0, 15, 500 μM IPTG) in the strain co-expressing psbAIp::luxAB and trcp::{ATG}kaiA. A constitutive nonspecific band is marked "nb." (B) Densitometry of the V. harveyi Lux abundance from the immunoblot in panel A, which was calculated from the ratio of Lux:nb abundance (1=Lux:nb at 0 μM IPTG). (C) KaiA enhances expression of heterologous hydrogenases. Immunoblot assays for expression of HynL, KaiA, and KaiC in strains of the wild type, RC41, and RC41 co-expressing trcp::{ATG}kaiA (i.e RC41/kaiA-OX) with (20 μM) or without IPTG (0 μM) for 24 hours. The top row shows both KaiA-enhanced and IPTG-induced expression of the large subunit (HynL, ~69 kDa) of the A. macleodii hydrogenase. "nb" denotes a nonspecific band recognized by the antisera raised against Thiocapsa roseopersicina HynL, which was used as an internal control for quantitative analyses of HynL expression levels. The $2^{nd}$ and $3^{rd}$ rows confirm the KaiA overexpression and its enhancement of the hyperphosphorylated KaiC expression in the RC41/kaiA-OX strain. The bottom row shows equivalent loading by CBB staining. Note that the kaiA overexpression construct with an ATG start codon is slightly "leaky" with a higher expression level as compared with WT even without IPTG induction. (D) Densitometry of expression levels of the *A. macleodii* hydrogenase subunit HynL from the top panel of (C). Ratios of the HynL/nb signals are averages with standard deviations from three experiments. **p<0.001 in a paired t-test. (E) Activity of the foreign *A. macleodii* hydrogenase in *S. elongatus*. After 24 h induction by 20 μM IPTG in light, the hydrogenase activities were determined. Data are the averages with S.D. from four independent experiments, and the hydrogenase activities in the RC41 and RC41/kaiA-OX strains were shown as ratios of the values as compared with wild type. (F) KaiA enhances accumulation of human proinsulin protein (GST::HPI fusion protein) in LD and LL (time 0=beginning of light; LD=12 h light/12 h dark cycle). Cells expressing conIIp::GST-HPI (GST-HPI/WT) or co-expressing conIIp::GST-HPI and trcp::{ATG}KaiA (GST-HPI/KaiA) were grown in the presence of 1 mM IPTG and collected at indicated LD and LL time points. The immunoblot assay for the fusion protein GST::HPI was performed using a monoclonal antibody against GST. "nb" denotes a nonspecific band recognized by the GST antibody. (G) Densitometry of the GST-HPI expression levels from the data of panel (F). Abscissa: black bar indicates the dark portion of a light/dark (LD) cycle, and the white bar indicates illumination in LD or LL. (H) Constant enhancement of the GST::HPI production by kaiA overexpression in DD. The LL-grown cells from the strains GST-HPI/WT or GST-HPI/KaiA were given a 12 h dark treatment, then 1 mM IPTG was applied at lights-on. After an additional 12 h growth in light, the cultures were transferred to constant darkness in a shaking water bath with bubbling and cells were collected every 6 h. "nb" denotes a nonspecific band recognized by the GST antibody. (I) Densitometry of the GST-HPI expression levels from two experiments in DD.

FIGS. 11A-11F provide graphs and images showing the application of kaiA manipulation to foreign gene expression. (A) Diagram of the trcp-driven expression cluster coding for the *A. macleodii* Deep Ecotype [NiFe] hydrogenase HynSL and 11 surrounding accessory proteins cloned into the NS I site of the endogenous hoxYH-knockout mutant (i.e. the RC41 strain). (B) Neither deletion of endogenous hoxYH genes nor overexpression of foreign *Alteromonas macleodii* hydrogenase cluster genes has a considerable effect on circadian luminescence rhythms. Luminescence rhythms in WT, ΔHOX, and RC41 strains in LL with or without IPTG application. Following a 12 h dark exposure to synchronize clocks among the cells in the population, luminescence rhythms were monitored in different strains with a psbAIp::luxAB reporter in NS II in LL. WT=wild type strain of the *S. elongatus* PCC 7942. ΔHOX=knock-out of endogenous hoxYH genes. RC41=*S. elongatus* ΔHOX mutant co-expressing *A. macleodii* hydrogenase cluster genes in NS I. (C) KaiA overexpression and its enhancement of KaiC expression in the hoxYH-null mutant strain co-expressing *A. macleodii* hydrogenase cluster genes and the kaiA-OX construct. WT (S.e. 7942)=wild type strain of the *S. elongatus* PCC 7942. RC41=HoxYH-knockout mutant co-expressing *A. macleodii* hydrogenase cluster genes. RC41+kaiA-OX=RC41 strain co-expressing trcp::{ATG}kaiA. KaiA and KaiC protein abundance levels in different strains with (20 μM) or without IPTG (0 μM) are shown in the upper and lower panels, respectively. (D-F) KaiA enhances expression of the GST-HPI fusion protein in constant light. (D) Diagram of the trcp-driven expression of the foreign coding fusion for the GST tag and human proinsulin. The linker sequence between GST and HPI is shown. (E) Immunoblot assay for the GST-HPI fusion protein was performed using a monoclonal antibody against GST. Cells expressing conIIp::GST-HPI (GST-HPI/WT) or co-expressing conIIp::GST-HPI & trcp::{ATG}kaiA (GST-HPI/KaiA) were grown in the presence of 1 mM IPTG and collected at the indicated time points in LL. The wild-type strain (WT) and transgenic strain expressing GST alone (GST/WT), grown in LL, were used as controls. "nb" denotes a nonspecific band in the same blot recognized by the GST antibody. (F) Densitometry of the GST-HPI expression levels from the panel of (E).

FIGS. 12A-12C provide graphs and a scheme showing complementary regulation by KaiA and KaiC and its manipulation to globally reprogram gene expression. (A) By constantly overexpressing kaiA (kaiA-OX), subjective dusk (Class I) genes are up-regulated (Class II subjective dawn genes are down-regulated) and rhythmicity of gene expression is lost. This gene expression pattern (curve) mimics that of subjective dusk genes (peak expression of the kaiBC gene) during the normal rhythm. Constant overexpression of kaiC (kaiC-OX) has the opposite effects on Class I vs. II gene expression and represses activity of subjective dusk genes. (B) These complementary gene expression patterns are mediated by the central circadian clock that is composed of a post-translational oscillator (PTO) that regulates the oscillation of KaiC phosphorylation status, leading to a Yin-Yang output of global gene expression (including kaiABC expression) where hyperphosphorylated KaiC up-regulates dusk (Class I) genes and hypophosphorylated KaiC up-regulates dawn (Class II) genes. Overexpression of kaiA vs. kaiC can lock the Yin-Yang patterns into either dusk phase (kaiA-OX) or dawn phase (kaiC-OX). The KaiABC PTO cycles the phosphorylation status of KaiC (hexamers) as regulated by interactions with KaiA (dimers) and KaiB (monomers). (C) Latching the Yin-Yang pattern into dusk phase by kaiA-OX enhances the expression of dusk genes— including heterologous genes inserted into NSI or NSII— and leads to a greater accumulation of gene products in constant light (LL) as shown by the cross-hatched area than would be possible if the same gene were expressed under control of the native rhythmic system.

Figures 1A, 1B, 1C, 1D:
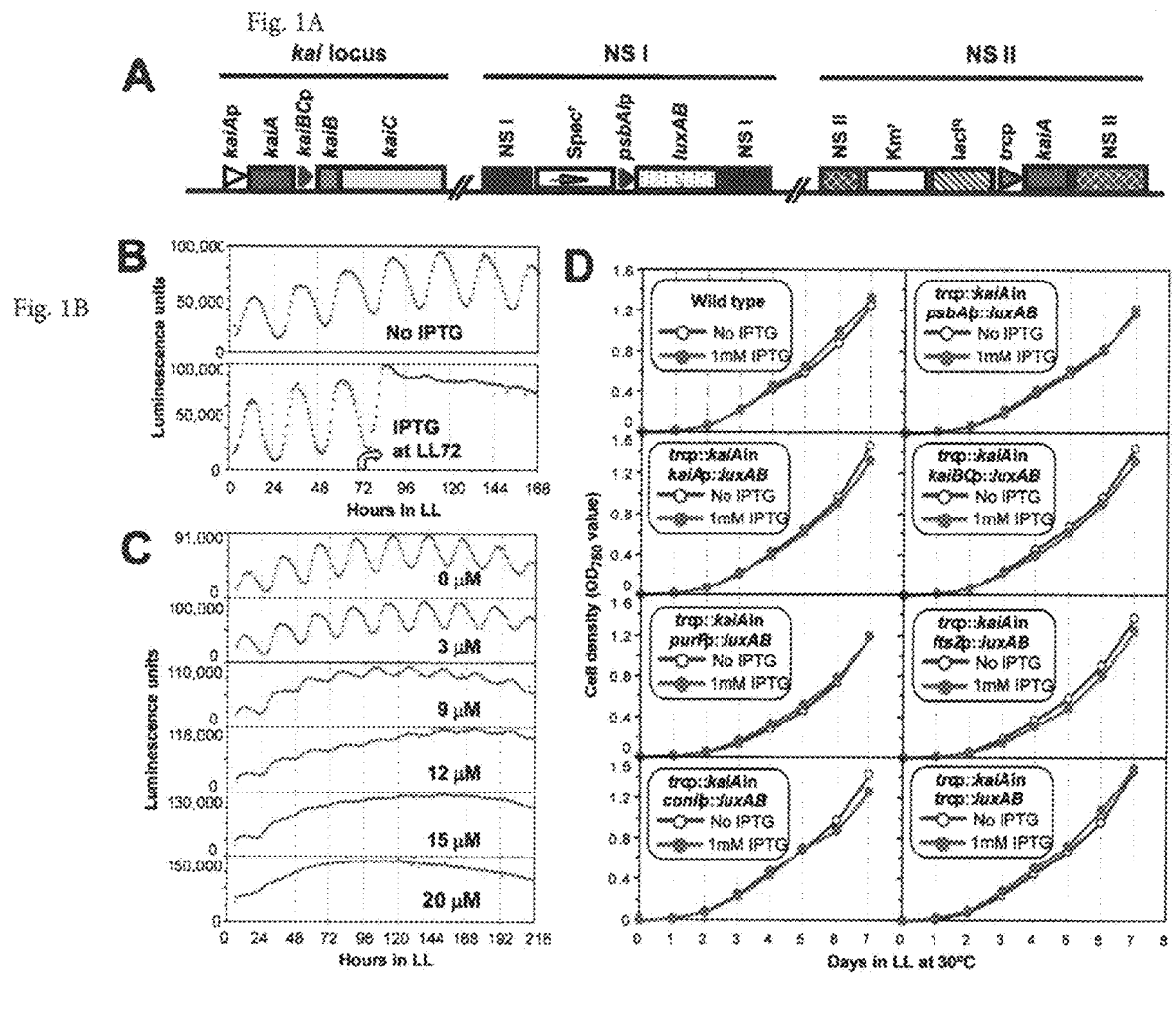
FIGS. 1A-1D provide a construct and graphs showing the acute responses of clock-controlled luminescence rhythm to kaiA-OX and its negligible effect on growth rate. (A) Constructs for luminescence reporting on the effect of kaiA expression as used in panels B and C of this figure. Diagram shows the intact kaiABC locus, the psbA1p::luxAB reporter construct in NSI, and the IPTG-derepressible trcp::kaiA expression cassette in NSII. (B) Rapid increase in luminescence expression following kaiA induction by IPTG at LL72 (=hour 72 in LL). (C) Dose response of kaiA-induced damping of the luminescence rhythms by varying IPTG concentrations. IPTG was added at time 0 of LL. (D) kaiA overexpression has no obvious effect on growth rate in various reporter strains as indicated. In presence or absence of IPTG, the cells were grown in LL at 30° C. with constant air bubbling and shaking. Cell densities were monitored by measuring $OD_{750}$ during growth. Data are averages from two independent experiments for each strain.

To illustrate the invention, several embodiments of the invention will now be described in more detail. Skilled artisans will recognize the embodiments provided herein have many useful alternatives that fall within the scope of the invention.

DETAILED DESCRIPTION OF THE INVENTION

The present invention provides a method of increasing gene expression by manipulating the circadian clock is that includes transforming a photosynthetic organism to include an expression control sequence that modulates the expression of a clock gene to increase expression of a target gene. Photosynthetic organisms having a modified circadian cycle reflecting this method are also described.

Definitions

Unless otherwise defined, all technical and scientific terms used herein have the same meaning as commonly understood by one of ordinary skill in the art to which this invention pertains. In case of conflict, the present specification will control.

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a," "an," and "the" are inclusive of their plural forms, unless contraindicated by the context surrounding such. The singular "plant" is likewise intended to be inclusive of the plural "plants."

The terms "comprising" and variations thereof do not have a limiting meaning where these terms appear in the description and claims.

The term "polynucleotide" or "nucleic acid molecule" refers to a polymeric form of nucleotides of at least 10 bases in length. The term includes DNA molecules (e.g., cDNA or genomic or synthetic DNA) and RNA molecules (e.g., mRNA or synthetic RNA), as well as analogs of DNA or RNA containing non-natural nucleotide analogs, non-native inter-nucleoside bonds, or both. The nucleic acid can be in any topological conformation. For instance, the nucleic acid can be single-stranded, double-stranded, triple-stranded, quadruplexed, partially double-stranded, branched, hairpinned, circular, or in a padlocked conformation.

The term "gene" as used herein refers to a nucleotide sequence that can direct synthesis of an enzyme or other polypeptide molecule (e.g., can comprise coding sequences, for example, a contiguous open reading frame (ORF) which encodes a polypeptide) or can itself be functional in the organism. A gene in an organism can be clustered within an operon, as defined herein, wherein the operon is separated from other genes and/or operons by intergenic DNA. Individual genes contained within an operon can overlap without intergenic DNA between the individual genes.

The term "polypeptide" encompasses both naturally-occurring and non-naturally-occurring proteins, and fragments, mutants, derivatives and analogs thereof. A polypeptide may be monomeric or polymeric. Further, a polypeptide may comprise a number of different domains each of which has one or more distinct activities.

The term "expression" when used in relation to the transcription and/or translation of a nucleotide sequence as used herein generally includes expression levels of the nucleotide sequence being enhanced, increased, resulting in basal or housekeeping levels in the host cell, constitutive, attenuated, decreased or repressed.

The term "vector" or "expression vector" refers to any type of genetic construct comprising a nucleic acid coding for a RNA capable of being transcribed. Expression vectors can contain a variety of control sequences, structural genes (e.g., genes of interest), and nucleic acid sequences that serve other functions as well.

The term "expression control sequence" as used herein refers to polynucleotide sequences which are necessary to affect the expression of coding sequences to which they are operatively linked. Expression control sequences are sequences which control the transcription, post-transcriptional events and translation of nucleic acid sequences. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (e.g., ribosome binding sites); sequences that enhance protein stability; and when desired, sequences that enhance protein secretion. The nature of such control sequences differs depending upon the host organism; in prokaryotes, such control sequences generally include promoter, ribosomal binding site, and transcription termination sequence. The term "control sequences" is intended to include, at a minimum, all components whose presence is essential for expression, and can also include additional components whose presence is advantageous, for example, leader sequences and fusion partner sequences.

The term "transformed," as used herein, refers to a cell into which has been introduced a nucleic acid molecule by molecular biology techniques. As used herein, the term transformation encompasses all techniques by which a nucleic acid molecule might be introduced into such a cell, including transfection with viral vectors, transformation with plasmid vectors, and introduction of naked DNA by electroporation, lipofection, and particle gun acceleration.

The term "recombinant," as used herein, refers to a nucleic acid is one that has a sequence that is not naturally occurring or has a sequence that is made by an artificial combination of two otherwise separated segments of sequence. This artificial combination can be accomplished by chemical synthesis or, more commonly, by the artificial manipulation of isolated segments of nucleic acids, e.g., by genetic engineering techniques.

The term "recombinant host cell" (or simply "host cell"), as used herein, is intended to refer to a cell into which a recombinant vector has been introduced. It should be understood that such terms are intended to refer not only to the particular subject cell but to the progeny of such a cell.

Because certain modifications may occur in succeeding generations due to either mutation or environmental influences, such progeny may not, in fact, be identical to the parent cell, but are still included within the scope of the term "host cell" as used herein. A recombinant host cell may be an isolated cell or cell line grown in culture or may be a cell which resides in a living tissue or organism.

A "transgenic photosynthetic organism," as used herein, refers to a photosynthetic organism (e.g., photosynthetic plant or bacteria) that contains recombinant genetic material not normally found in organisms of this type and which has been introduced into the organism in question (or into progenitors of the plant) by human manipulation. Thus, for example, a plant that is grown from a plant cell into which recombinant DNA is introduced by transformation is a transgenic plant, as are all offspring of that plant that contain the introduced transgene (whether produced sexually or asexually).

The term "operably linked" refers to the arrangement of various polynucleotide elements relative to each other such that the elements are functionally connected and are able to interact with each other. Such elements may include, without limitation, a promoter, an enhancer, a polyadenylation sequence, one or more introns and/or exons, and a coding sequence of a gene of interest to be expressed. "Operably linked" expression control sequences refers to a linkage in which the expression control sequence is contiguous with the gene of interest to control the gene of interest, as well as expression control sequences that act in trans or at a distance to control the gene of interest.

The term "modulation" means in relation to expression or gene expression, a process in which the expression level is changed by said gene expression in comparison to the control organism, the expression level may be increased or decreased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased expression of a target gene.

Methods of Increasing Gene Expression by Manipulating the Circadian Clock

In one aspect, the invention provides a method of increasing gene expression by manipulating the circadian clock. The method includes transforming a photosynthetic organism to include an expression control sequence that modulates the expression of a clock gene to increase expression of a target gene.

Expression of the target gene can be increased in two different ways. In some embodiments, the expression of the target gene is operably linked to expression of the clock gene. For example, expression of the clock gene can increase the activity of a promoter associated a target gene. In any case, in these embodiments, increased or decreased expression of the clock gene has a relatively direct effect on increasing expression of the target gene.

In another embodiment, modulating expression of a clock gene suppresses the circadian rhythm of the photosynthetic organism. The circadian rhythm is a cyclic pattern of activity for the photosynthetic organism, which reflects the modulation of gene expression occurring in response to operation of the circadian clock. By suppressing the circadian rhythm, the photosynthetic organism can be "locked" into a single state, in which expression of the target gene is occurring at a high state. In this embodiment, expression of the target gene is not necessarily operably linked to expression of the clock gene, but rather is effected by the overall state of the cell, with regard to its position in the circadian cycle.

The expression control sequence is a polynucleotide sequence that modulates the expression of a clock gene. An example of an expression vector including an expression control sequence is shown in FIG. 1A. Preferably, the expression vector or vectors include an expression control sequence to increase expression of a clock gene, the clock gene whose expression is being increased, and other sequences known to those skilled in the art for use in expression vectors, such as selection markers. The expression vectors shown in FIG. 1A are flanked with neutral site (NS I and NS II) sequences to allow for homologous recombination into neutral site I (GenBank accession number U30252) or neutral site II (GenBank accession number U44761), which are sites where the *S. elongates* chromosome can be disrupted without any discernible effect on the phenotype. Vectors used for these neutral sites include the NS 1 vector pAM1303 (SEQ ID NO: 1) and the NS 2 vector pAM1579 (SEQ ID NO: 2), shown in FIG. 1.

A clock gene is a gene in an organism such as a photosynthetic organism that is involved in regulation of the circadian rhythm. Because photosynthetic organisms in particular thrive when they optimize the metabolism to the ups and downs of the daily cycle set by the sun, clock genes play an important role in photosynthetic organisms. See Johnson C. H., Annu Rev Physiol. 63:695-728 (2001). For a review of bacterial circadian programs, see Johnson C. H., Cold Spring Harb Symp Quant Biol. 72:395-404 (2007).

The specific clock genes involved in regulating the circadian rhythm can differ in different types of photosynthetic organisms. Accordingly, in some embodiments, the clock genes are plant clock genes. In further embodiments, the plant clock genes are algal clock genes. In other embodiments, the clock genes are photosynthetic bacteria clock genes. In a yet further embodiment, the clock genes are cyanobacterial clock genes. The specific clock genes for particular organisms are known to those skilled in the art.

In some embodiments, the clock gene is selected from the group consisting of KaiA (SEQ ID NO: 3), KaiB (SEQ ID NO: 4), and KaiC (SEQ ID NO: 5), and homologs thereof. These genes are part of the gene cluster kaiABC that control the circadian rhythm in cyanobacteria. See GenBank number AB010691, and Ishiura et al., Science 281, 1519-1523 (1998). For example, in some embodiments, the clock gene is KaiA or KaiC and the clock gene is overexpressed.

Other plant clock genes are known to those skilled in the art. TOC1 is a clock gene identified in *Arabidopsis*. Transient induction of TOC1 expression with ethanol using an ALC::TOC1 line caused upregulation of 1254 output genes. Gendron et al., PNAS, 109(8):3167-72 (2012). Another *Arabidopsis* clock gene is CCA1. Nagel et al. overexpressed CCA and analyzed RVE1 and HEMA1 expression. RVE1 has an increase in expression at some specific phases under LD conditions. Nagel et al., PNAS, 112(34):E4802-10 (2015). Another *Arabidopsis* clock gene is PRR7. Liu et al., 2013, shows that the triple mutant prr5 prr7 prr9 constitutively upregulate cold-stress inducible genes such as CBF2 and CBF3. Liu et al., Plant J. 76(1):101-14 (2013). The prr5/prr7/prr9 mutant also shows upregulation of day genes and dowregulation of night genes. Nakamichi et al., Plant Cell Physiol., Plant Cell Physiol. 50(3):447-62 (2009).

In other embodiments, the term "clock gene" can also include genes involved in the transmission of signals from clock genes to other genes. For example, in cyanobacteria, genes encoding proteins involved in the transmission of signals from clock genes include RpaA, RpaB, SasA, and ΔCikA, and homologs thereof. For clarity sake, these additional genes can be referred to as signal-transmitting clock genes. In some embodiments, the expression of a target gene can be increased by modulating the activity of one of these signal-transmitting clock genes. For example, in some embodiments the clock gene is ΔCikA, and expression of the clock gene is eliminated or suppressed.

Specific polynucleotides/genes useful in the methods and compositions of the invention are described herein. However, it should be recognized that absolute identity to such genes is not necessary, as substantially similar polynucleotides/genes that perform substantially similar functions can also be used in the compositions and methods of the present disclosure. For example, changes in a particular gene or polynucleotide containing a sequence encoding a polypeptide or enzyme can be performed and screened for activity. Typically such changes include conservative mutation and silent mutations. Such modified or mutated polynucleotides and polypeptides can be screened for expression or function of enzymes using methods known in the art. Additionally, homologs of the polynucleotides/genes of the present disclosure are suitable for use in the compositions and methods disclosed herein.

Due to the inherent degeneracy of the genetic code, polynucleotides which encode substantially the same or a functionally equivalent polypeptide can also be used to clone and express the same polypeptides or enzymes. As will be understood by those of skill in the art, it can be advantageous to modify a coding sequence to enhance its expression in a particular host. The genetic code is redundant with 64 possible codons, but most organisms typically use a subset of these codons. The codons that are utilized most often in a species are called optimal codons, and those not utilized very often are classified as rare or low-usage codons.

Those of skill in the art will recognize that, due to the degenerate nature of the genetic code, a variety of DNA compounds differing in their nucleotide sequences can be used to encode a given polypeptide. The present disclosure includes DNA compounds of any sequence that encode the amino acid sequences of the polypeptides described herein. In similar fashion, a polypeptide can typically tolerate one or more amino acid substitutions, deletions, and insertions in its amino acid sequence without loss or significant loss of a desired activity.

Homologs of genes or proteins are encompassed by the photosynthetic organisms and methods provided herein. The term "homologs" used with respect to an original polypeptide or gene of a first family or species refers to distinct enzymes or genes of a second family or species which are determined by functional, structural or genomic analyses to be a polypeptide or gene of the second family or species which corresponds to the original polypeptide or gene of the first family or species. Most often, homologs will have functional, structural or genomic similarities. Techniques are known by which homologs of a gene or polypeptide can readily be cloned using genetic probes and PCR. Homologs can be identified by reference to various databases and identity of cloned sequences as homolog can be confirmed using functional assays and/or by genomic mapping of the genes.

A protein has "homology" or is "homologous" to a second protein if the nucleic acid sequence that encodes the protein has a similar sequence to the nucleic acid sequence that encodes the second protein. Alternatively, a protein has homology to a second protein if the two proteins have "similar" amino acid sequences. Thus, the term "homologous proteins" is defined to mean that the two proteins have similar amino acid sequences.

As used herein, two proteins (or a region of the proteins) are substantially homologous when the amino acid sequences have at least about 30%, 40%, 50% 60%, 65%, 70%, 75%, 80%, 85%, 90%, 91%, 92%, 93%, 94%, 95%, 96%, 97%, 98%, or 99% identity. Similarly, two polynucleotides (or a region of the polynucleotides) are substantially homologous when the nucleic acid sequences have at least about 30%, 40%, 50% 60%, 65%, 70%, 75%, 80%, 85%, 90%, 91%, 92%, 93%, 94%, 95%, 96%, 97%, 98%, or 99% identity. To determine the percent identity of two amino acid sequences, or of two nucleic acid sequences, the sequences are aligned for optimal comparison purposes (e.g., gaps can be introduced in one or both of a first and a second amino acid or nucleic acid sequence for optimal alignment and non-homologous sequences can be disregarded for comparison purposes). The amino acid residues or nucleotides at corresponding amino acid positions or nucleotide positions are then compared. When a position in the first sequence is occupied by the same amino acid residue or nucleotide as the corresponding position in the second sequence, then the molecules are identical at that position (as used herein amino acid or nucleic acid "identity" is equivalent to amino acid or nucleic acid "homology"). The percent identity between the two sequences is a function of the number of identical positions shared by the sequences, taking into account the number of gaps, and the length of each gap, which need to be introduced for optimal alignment of the two sequences.

The term "increased expression" or "overexpression" as used herein means any form of expression that is additional to the original wild-type expression level. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a nucleic acid encoding the polypeptide of interest. For example, endogenous promoters may be altered in vivo by mutation, deletion, and/or substitution (see U.S. Pat. No. 5,565,350 and International Publication WO9322443), or isolated promoters may be introduced into a cell of a photosynthetic organism in the proper orientation and distance from a gene of the present invention so as to control the expression of the gene.

Reference herein to "decreased expression" or "reduction or elimination" of expression is taken to mean a decrease in endogenous gene expression and/or polypeptide levels and/or polypeptide activity relative to control organisms. This reduction or substantial elimination of expression may be achieved using routine tools and techniques. The reduction or substantial elimination is in increasing order of preference at least 10%, 20%, 30%, 40% or 50%, 60%, 70%, 80%, 85%, 90%, or 95%, 96%, 97%, 98%, 99% or more reduced compared to that of control organisms.

Decreased expression can result from a functional deletion, including a mutation, partial or complete deletion, insertion, or other variation made to a gene sequence or a sequence controlling the transcription of a gene sequence, which reduces or inhibits production of the gene product, or renders the gene product non-functional. In some instances a functional deletion is described as a knockout mutation. Decreased expression can also includes amino acid sequence changes by altering the nucleic acid sequence, placing the gene under the control of a less active promoter, down-regulation, expressing interfering RNA, ribozymes or antisense sequences that target the gene of interest, or through any other technique known in the art. In one example, the sensitivity of a particular enzyme to feedback inhibition or inhibition caused by a composition that is not a product or a reactant (non-pathway specific feedback) is lessened such that the enzyme activity is not impacted by the presence of a compound. In other instances, an enzyme that has been altered to be less active can be referred to as attenuated.

A "deletion" is the removal of one or more nucleotides from a nucleic acid molecule or one or more amino acids from a protein, the regions on either side being joined together.

A "knock-out" is a gene whose level of expression or activity has been reduced to zero. In some examples, a gene is knocked-out via deletion of some or all of its coding sequence. In other examples, a gene is knocked-out via introduction of one or more nucleotides into its open-reading frame, which results in translation of a non-sense or otherwise non-functional protein product.

Another method for the reduction or substantial elimination of expression of a clock gene is by introducing and expressing in a photosynthetic organism a genetic construct into which the nucleic acid (in this case a stretch of substantially contiguous nucleotides derived from the gene of interest, or from any nucleic acid capable of encoding an ortholog, paralog or homolog of any one of the protein of interest) is cloned as an inverted repeat (in part or completely), separated by a spacer (non-coding DNA). This results in RNA-mediated silencing of the gene.

In some embodiments, clock gene expression is increased by including a promoter that is operably linked to the clock gene. The term "promoter" refers to a nucleic acid sequence that regulates, either directly or indirectly, the transcription of a corresponding nucleic acid coding sequence to which it is operably linked. The promoter may function alone to regulate transcription, or, in some cases, may act in concert with one or more other regulatory sequences such as an enhancer, silencer, or transcription factor to regulate transcription of the transgene. When the promoter is acting in conjunction with other factors such as a transcription factor, it is referred to herein as a promoter system. The promoter comprises a DNA regulatory sequence, wherein the regulatory sequence is derived from a gene, which is capable of binding RNA polymerase and initiating transcription of a downstream (3'-direction) coding sequence.

A promoter generally comprises a sequence that functions to position the start site for RNA synthesis. The best-known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. The spacing between promoter elements frequently is flexible, so that promoter function is preserved when elements are inverted or moved relative to one another To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA. Alternative ribosome binding sites, such as the IRES elements (internal ribosome entry sites), can also be used as sites for control of expression.

A promoter may be one naturally associated with a nucleic acid sequence, as may be obtained by isolating the 5' non-coding sequences located upstream of the coding segment and/or exon. Such a promoter can be referred to as "endogenous." Alternatively, certain advantages may be gained by positioning the coding nucleic acid segment under the control of a recombinant or heterologous promoter, which refers to a promoter that is not normally associated with a nucleic acid sequence in its natural environment. Such promoters may include promoters of other genes, and promoters isolated from any virus, or prokaryotic or eukaryotic cell, and promoters not "naturally occurring," i.e., containing different elements of different transcriptional regulatory regions, and/or mutations that alter expression. Furthermore, it is contemplated the control sequences that direct transcription and/or expression of sequences within non-nuclear organelles such as mitochondria, chloroplasts, and the like, can be employed as well.

In some embodiments, the promoter is an inducible promoter. In some embodiments, the promoter is a constitutive promoter. As used herein, "inducible promoter" refers to a promoter that drives expression of a polynucleotide to which it is operably linked upon cellular perception of a stimulus. Likewise, inducible promoters can terminate expression of a polynucleotide to which it is operably linked upon removal of a stimulus. An example of an inducible promoter in the present disclosure is the isopropyl-β-D-thiogalactoside (IPTG) inducible promoter, in which this promoter drives expression of a polynucleotide to which it is operably linked upon perception of IPTG, an exogenous chemical. Any appropriate inducible promoter that has use in the compositions and methods of the present disclosure may be used accordingly. One of skill in the art will recognize that many characterized inducible promoters exist and can be used according to the compositions and methods disclosed herein. Constitutive promoters, on the other hand, are those promoters that are substantially insensitive to regulation by external stimuli and promote expression of a given polynucleotide in an essentially constant manner.

Increased Expression of a Target Gene

The present invention includes modulating the expression of a clock gene to increase expression of a target gene. A wide variety of target genes can be used within the scope of the present invention. In some embodiments, the target gene is an endogenous gene, while in other embodiments the target gene is a heterologous gene. Preferably the target gene is a gene capable of expressing a polypeptide. When the target gene is a heterologous gene, the photosynthetic organism will be, by definition, a transgenic photosynthetic organism.

In some embodiments, the target gene is a gene influencing the expression of a biofuel product or biofuel precursor. A target gene influencing the expression of a biofuel product or biofuel precursor can be either an endogenous gene or a heterologous gene. A wide variety of photosynthetic organisms naturally express biofuel products or precursors as a part of their regular metabolism, through the expression of endogenous genes. However, in other cases, photosynthetic organisms are transformed through the incorporation of heterologous genes. See for example US 2014/0186877, which describes engineered microorganisms including an alpha-olefin-associated enzyme is incorporated into cyanobacteria to increase 1-alkene production.

A "biofuel" as used herein is any fuel that derives from a biological source. A "fuel" refers to one or more hydrocarbons, one or more alcohols, one or more fatty esters or a mixture thereof. Preferably, liquid hydrocarbons are used.

"Biofuel precursors," as used herein, refer to lipids and oils produced by algae that are organic compounds suitable for use in preparing a biofuel. While the lipids and oils will typically require additional processing before being used as biofuels, in some instances they may be used directly without additional processing. Lipids, as defined herein, include naturally occurring fats, waxes, sterols, monoglycerides, diglycerides, triglycerides, and phospholipids. The preferred lipids are fatty acid lipids found in triacylglycerides. Free fatty acids are synthesized in algae through a biochemical process involving various enzymes such as trans-enoyl-acyl carrier protein (ACP), 3-hydroxyacyl-ACP. 3-ketoacyl-ACP, and acyl-ACP. Examples of free fatty acids include fatty acids having a chain length from 14 to 20, with varying degrees of unsaturation. A variety of lipid-derived compounds can also be useful as biofuel and may be extracted from oleaginous algae. These include isoprenoids, straight chain alkanes (with short (3-7 carbon) and medium (8 to 12 carbon) chain lengths), and long and short chain alcohols, such short chain alcohols including ethanol, butanol, and isopropanol.

While biofuel is an example of a product whose expression can be increased as a result of increased expression of either endogenous or heterologous gene expression, in some embodiments, the invention is directed solely to increased expression of an endogenous gene. Examples of endogenous genes that can be readily influenced by manipulating the circadian clock of a photosynthetic organism include "Class I"/"subjective dusk" genes, which activate at down and risk throughout the day to peak expression at dusk, and "Class II/"subjective dawn" genes, which activate at night and peak at dawn. The inventors have identified a large number of genes that respond to the circadian clock, and have shown that KaiC overexpression represses the predominant Class I dusk genes, while up-regulating Class II dawn genes, while KaiA overexpression acts in the opposite manner, in a "Yin-Yang" interdependency.

In other embodiments, the invention is directed solely to increased expression of a heterologous gene. Preferably, the heterologous gene is a gene capable of expressing a protein, and in particular a protein having practical value, such as a medically or industrially useful protein. Examples of proteins that have been recombinantly expressed include chymosin, human insulin, human growth hormone, blood clotting factor VIII, hepatitis B vaccine, and hydrogenase. In particular, work by the inventors have demonstrated manipulating the circadian clock to increase expression of hydrogenase and pro-insulin.

Photosynthetic Organisms Having a Modified Circadian Cycle

Another aspect of the invention provides a photosynthetic organism having a modified circadian cycle. The circadian cycle is modified by transforming a photosynthetic organism to include an expression control sequence that modulates the expression of a clock gene to increase expression of a target gene. The presence of a circadian cycle appears to be nearly universal, occurring not only in all plants thus far examined, but also in insects and microbes.

In some embodiments, the photosynthetic organism is a plant. Circadian rhythms control many aspects of plant metabolism, physiology and development. Plants make use of environmental signals such as the daily light-dark cycle or regular temperature variations to maintain a biological timekeeping mechanism. This mechanism, known as the circadian clock, is commonly represented as a so-called oscillator that consists of a set of proteins which interact in a complex pattern of positive and negative transcriptional feedback loops, for a review see McClung, C. R., Plant Cell 18, 792-803, 2006. The oscillator is calibrated by external signals (such as light, perceived by phytochromes and cryptochromes) which are transmitted via the "input pathways" to the oscillator. The oscillator on its turn controls a number of pathways (the "output pathways") which regulate physiological processes that are influenced by the daily environmental changes. An overview is given in Barak et al., Trends in Plant Science 5, 517-522, 2000, and include for example induction of flowering, opening of petals, opening or closure of stomata, growth of the hypocotyl, movement of cotyledons and leaves, movement of chloroplasts, expression of genes associated with photosynthesis and related biochemical and physiological processes, cytoplasmic calcium concentrations, and the phosphorylation status of proteins like phosphoenol pyruvate carboxylase. For example, modulating expression of a nucleic acid encoding a HUB1 (Histone Monoubiquitination 1) has been shown to alter various growth characteristics in a plant. See U.S. Pat. No. 9,074,006.

Expression of the circadian clock proteins may be modified in a wide range of higher plants to confer altered circadian clock and/or photoperiodism function, including monocotyledonous and dicotyledenous plants. These include, but are not limited to, *Arabidopsis, Cardamine,* cotton, tobacco, maize, wheat, rice, barley, soybean, beans in general, rape/canola, alfalfa, flax, sunflower, safflower, brassica, cotton, flax, peanut, clover; vegetables such as lettuce, tomato, cucurbits, cassava, potato, carrot, radish, pea, lentils, cabbage, cauliflower, broccoli, Brussels sprouts, peppers; tree fruits such as citrus, apples, pears, peaches, apricots, walnuts; other trees including poplar, oak, maple, pine, spruce and other conifers; and flowers or other ornamental plants such as carnations, roses, petunias, orchids, *impatiens*, pansies, lilies, snapdragons, geraniums, and so forth.

In some embodiments, the photosynthetic organism is algae. A wide variety of algae are suitable for genetic modification. Among these are dinoflagellates (e.g., *Ampidinium, Symbidinium*), diatoms (e.g., *Phaeodactylum, Cyclotella, Navicula, Cylindrotheca, Thalassiosira*), green algae (e.g. *Chlamydomonas, Chlorella, Haematococcus, Dunaliella, Ostreococcus, Coccomyxa*), red algae (e.g., *Porphyridium, Kappaphycus, Galdieria*), macroalgae (e.g., *Ulva*), and bluegreen algae (e.g., *Synechocystis, Synechococcus, Anabaena, Nostoc*). The methods and protocols have been described in the literature and are incorporated here by reference (Leon & Fernandez, Advances in Experimental Medicine and Biology, Ch. 1, 616 1-129 (2007)); Packer & Glazer, Meth Enzymol 167, p. 1-910 (1988); Bryant, The molecular biology of Cyanobacteria. Advances in Photosynthesis, Kluwer Academic Publishers. 880 pp (1994)).

For example, the algae that are genetically modified can be selected from the group consisting of cyanophyta, rhodophyta, heterokontophyta, haptophyta, cryptophyta, dinophyta, euglenophyta, and chlorophyta. The genetically modified alga can also be a species selected from the group consisting of *Chlamydomonas* sp., *Chlorella* sp., *Nannochloropsis* sp., *Synechocystis* sp., *Synechococcus, Anabaena* sp., *Cyclotella, Phaeodactylum* sp., *Crypthicodineum* sp., *Ulkenia, Schizochytridum* sp., *Haematococcus* sp., *Arthrospira* (*Spirulina*) sp., *Galdieria* sp., *Ostreococcus* sp., *Coccomyxa* sp. and *Dunaliella* sp.

Methods for the transformation of various types of algae are known to those skilled in the art. See for example Radakovits et al., Eukaryotic Cell, 9, 486-501 (2010), which is incorporated herein by reference. The transformation of the chloroplast genome was the earliest method and is well documented in the literature (Kindle et al., Proc Natl Acad Sci., 88, p. 1721-1725 (1991)). A variety of methods have been used to transfer DNA into microalgal cells, including agitation in the presence of glass beads or silicon carbide whiskers, electroporation, biolistic microparticle bombardment, and *Agrobacterium tumefaciens*-mediated gene transfer. A preferred method of transformation for the present invention is biolistic microparticle bombardment, carried out with a device referred to as a "gene gun."

In other embodiments, the photosynthetic organism is a photoautotrophic or photoheterotrophic bacteria. Photoautotrophic and photoherotrophic bacteria are bacteria that derive at least part of their energy from photosynthesis. Photoautotrophic bacteria derive their energy exclusively from light, whereas photoheterotrophic bacteria are organisms that use light for energy, but cannot use carbon dioxide as their sole carbon source, and therefore use organic compounds from the environment to satisfy their carbon requirements.

Because of their increased dependence on solar energy, and the associated need for circadian regulation, photoautotrophic bacteria are of particular interest for use in the present invention. Photoautotrophic bacteria are typically Gram-negative rods which obtain their energy from sunlight through the processes of photosynthesis. In this process, sunlight energy is used in the synthesis of carbohydrates, which in recombinant photoautotrophs can be further used as intermediates in the synthesis of biofuels. In other embodiment, the photoautotrophs serve as a source of carbohydrates for use by nonphotosynthetic microorganism (e.g., recombinant *E. coli*) to produce biofuels by a metabolically engineered microorganism. Certain photoautotrophs called anoxygenic photoautotrophs grow only under anaerobic conditions and neither use water as a source of hydrogen nor produce oxygen from photosynthesis. Other photoautotrophic bacteria are oxygenic photoautotrophs. These bacteria are typically cyanobacteria. They use chlorophyll pigments and photosynthesis in photosynthetic processes resembling those in algae and complex plants. During the process, they use water as a source of hydrogen and produce oxygen as a product of photosynthesis (see, e.g. US 2011/0250060).

In some embodiments, the present invention provides cyanobacteria that contain an expression control sequence for manipulating the circadian clock. Cyanobacteria include various types of bacterial rods and cocci, as well as certain filamentous forms. The cells contain thylakoids, which are cytoplasmic, platelike membranes containing chlorophyll. In some embodiments, the cyanobacteria are a *Synechococcus* sp. In some embodiments, the *Synechococcus* sp. is *Synechococcus elongatus*. In some embodiments, the *Synechococcus elongatus* is *Synechococcus elongatus* PCC7942. One of skill in the art will recognize that other cyanobacteria can be used according to the present disclosure. Examples of other exemplary cyanobacteria include marine cyanobacteria such as *Synechococcus* sp. WH8102, thermostable cyanobacteria such as *Thermosynechococcus elongatus* BP-1, photoheterotrophic cyanobacteria such as *Synechocystis* sp. PCC6803 and filamentous cyanobacteria such as *Nostoc punctiforme*.

The following examples have been included to more clearly describe particular embodiments of the invention. However, there are a wide variety of other embodiments within the scope of the present invention, which should not be limited to the particular examples provided herein.

EXAMPLES

Example 1

Circadian Yin-Yang Regulation and its Manipulation to Globally Reprogram Gene Expression The cyanobacterial circadian program exerts genome-wide control of gene expression. KaiC undergoes rhythms of phosphorylation that are regulated by interactions with KaiA and KaiB. The phosphorylation status of KaiC is thought to mediate global transcription via output factors SasA, CikA, LabA, RpaA, and RpaB. Overexpression of kaiC has been reported to globally repress gene expression.

The inventors show that the positive circadian component KaiA upregulates "subjective dusk" genes and its overexpression de-activates rhythmic gene expression without significantly affecting growth rates in constant light. The global patterns of expression that are regulated by KaiA versus KaiC were analyzed, and it was found, in contrast to the previous report of KaiC repression, that there is a "Yin-Yang" regulation of gene expression whereby kaiA overexpression activates "dusk genes" and represses "dawn genes," whereas kaiC overexpression complementarily activates "dawn genes" and represses "dusk genes." Moreover, continuous induction of kaiA latched KaiABC-regulated gene expression to provide constitutively increased transcript levels of diverse endogenous and heterologous genes that are expressed in the predominant "subjective dusk" phase. In addition to analyzing KaiA regulation of endogenous gene expression, these insights were applied to the expression of heterologous proteins whose products are of potential value, namely human proinsulin, foreign luciferase, and exogenous hydrogenase.

Both KaiC and KaiA complementarily contribute to the regulation of circadian gene expression via Yin-Yang switching. Circadian patterns can be reprogrammed by overexpression of kaiA or kaiC to constitutively enhance gene expression, and this reprogramming can improve 24/7 production of heterologous proteins that are useful as pharmaceuticals or biofuels.

Experimental Procedures

Figure 9A:
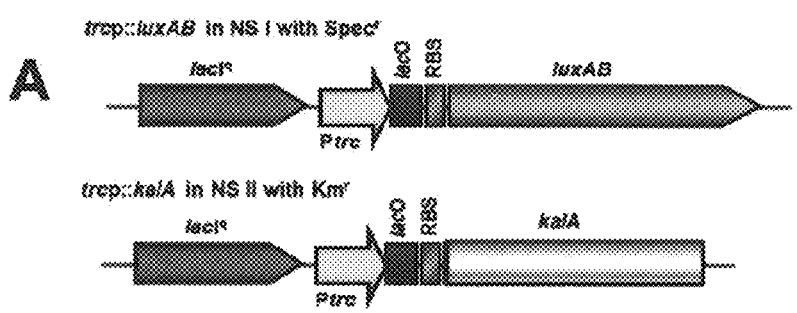
FIGS. 9A and 9B provide a diagram and graphs showing the additional enhancement of the IPTG-inducible trc promoter by kaiA overexpression. (A) Diagram of the trc/kaiA strain coexpressing trcp::kaiA in NS II with a kanamycin resistance marker and trcp::luxAB reporter in NS I with a spectinomycin resistance marker. (B) Luminescence expression profiles were compared between strain harboring the trcp::luxAB reporter and strain co-expressing both the trcp::luxAB reporter and trcp::kaiA in the absence (No IPTG) or presence of 1 mM IPTG added at LL0.

Promoter/reporter constructs. *Vibrio harveyi* luciferase encoded by luxA and luxB (luxAB) genes was used as a luminescence reporter of expression activities from various promoters from either *Escherichia coli* or *Synechococcus elongatus* PCC 7942. The kaiAp::luxAB expression cassette was made by fusing a 0.24 kb upstream fragment (produced from Dra I/Eag I cleavage) of the kaiA gene to luxAB and then inserted into the EcoRV site of a neutral site II vector pAM1579 that includes a kanamycin selection marker ($Km^r$). A 260-bp PCR fragment covering the 5' upstream portion of the *E. coli* σ70 binding site gene conII and a 300-bp PCR fragment containing the upstream region of the purine biosynthesis pathway gene purF were respectively cloned into the Not I/BamH I site of a promoterless luxAB vector pAM1414 to give rise to conIIp::luxAB and purFp::luxAB reporters in NS I. A 2.44-kb DNA fragment harboring luxAB coding regions was inserted into the Nde I site of the neutral site I expression vector pTrc-NS I with a spectinomycin resistance ($Spec^r$) marker to make the trcp::luxAB reporter construct, in which the expression of luxAB genes was under the control of an IPTG (isopropyl β-D-1-thiogalactopyranoside)-inducible trc promoter that is regulated by the repressor $lacI^q$. (FIG. 9A). Construction of other reporters was described previously, including kaiBCp::luxAB in NS I (Xu et al., EMBO J. 22, 2117-2126 (2003)), fisp::luxAB (chloramphenicol resistance, Cm$^r$) in NS I (Min et al., J. Biol. Rhythm. 19, 103-112 (2004)), ftsZp::luxAB (Km$^r$) in NS II (Mori, T., and Johnson, C. H., J. Bacteriol. 183, 2439-2444 (2001)), and psbAIp::luxAB (Spec$^r$) in NS I (Kondo et al., Proc. Natl. Acad. Sci. USA 90, 5672-5676 (1993)).

Generation of kaiA-overexpressing strains. To "reprogram" the circadian regulation of global gene expression in different reporter backgrounds, three versions of IPTG-derepressible kaiA-expressing constructs were used. The first one used the open reading frame (positions +1~825) of wild-type kaiA (GTG translation start codon) with its 5'- and 3'-flanking sequences (from −27 to −1 and from +826 to +905) cloned into the downstream EcoR I/Xba I site of the trc promoter on pTrc-NS I to make the construct trcp::kaiA in NS I with a Spec$^r$ selection marker. The second version was a trcp::kaiA fusion into NS II with a Km$^r$ selection marker. Kutsuna et al., J. Bacteriol. 189, 7690-7696 (2007). The third version was the trc promoter-driven kaiA coding region with an ATG translation start codon [trcp::{ATG}kaiA] located in NS II with a Km$^r$ marker. These versions of kaiA-expressing constructs were introduced into appropriate reporter strains or foreign gene-expressing strains via double homologous recombination. For induction of the trcp-driven (WT)kaiA or {ATG}kaiA expression, the indicated concentration of IPTG or an equivalent volume of water (as control) was administered to the liquid cultures or under the agar medium as specified. For the kaiA-overexpressing strains used in this study, they were all (WT)kaiA versions unless {ATG}kaiA is specifically indicated.

Foreign gene-expressing strains. Generation of the cyanobacterial RC41 strain that expresses the gene cluster encoding *A. macleodii* Deep Ecotype [NiFe] hydrogenase HynSL and other 11 surrounding accessory proteins in NS I was described previously (Weyman et al., PLoS ONE 6, e20126 (2011)), in which the endogenous cyanobacterial hoxYH genes encoding the bidirectional [NiFe] hydrogenase (HoxYH) were deleted. To make a strain expressing a fusion protein between glutathione S-transferase (GST) and human proinsulin (HPI), the HPI coding sequence from a human cDNA clone BC005255 (OriGene, Rockville, Md.) was fused to the C-terminal EcoR I site of the GST tag from the vector pGEX-6P-1 (GE Healthcare Bio-Sciences Corp., Piscataway, N.J.). A PCR fragment containing the GST-HPI fusion with a linker was cloned downstream of the conII promoter. After confirmation of the construct with a Spec$^r$ marker and by DNA sequencing, the conIIp::GST-HPI expression cassette was introduced into the NS I site.

Growth conditions and luminescence measurements. The cyanobacterium *S. elongatus* PCC 7942 was grown in modified BG11 liquid media with air bubbling or on BG11 agar plates supplemented with appropriate antibiotics (spectinomycin, 40 μg/ml; kanamycin, 10 μg/ml; erythromycin, 5 μg/ml; chloramphenicol, 7.5 μg/ml) at 30° C. under continuous cool-white illumination (LL) (50 μE/m$^2$ s). Bustos et al., J. Bacteriol. 173, 7525-7533 (1991). Before the cells were released into LL, 1~2 cycles of the 12 hr/12 hr light/dark (LD) were given to synchronize the cultured cells. In vivo luminescence assays in cyanobacteria were performed as described previously for liquid cultures (3 vials each sample) or for colonies on agar (12 colonies each sample). For luminescence assays in *E. coli*, 20 μl of 1% n-decanal was mixed with 0.5 ml of cells at OD$_{600}$=0.5, and the total luciferase activities were immediately measured with FB12 Luminometer (Zylux Corporation, Germany). Growth rates of cyanobacterial strains were determined in a temperature-controlled shaking water bath with shaking at 100 rpm and with air bubbling into the cultures. Initial cultures were grown in liquid BG-11 medium at 30° C. under constant illumination (50 μE/m$^2$ s) in a shaking water bath at 100 rpm and with air bubbling into the cultures. Cell densities were monitored by measuring the optical density at 750 nm (OD$_{750}$). When cell densities reached OD$_{750}$~0.8, cultures were diluted to OD$_{750}$~0.005, and grown in LL in water baths set to 30° C. with shaking (100 rpm) and air bubbling in presence or absence of IPTG. Cell densities were determined at OD$_{750}$ over a time course as indicated. When OD$_{750}$ values of cell cultures exceed 0.9, the OD measurement is not linear with cell density. Therefore, for samples with an OD$_{750}$ that was larger than 0.9, the samples were diluted to an OD$_{750}$ that was within the linear range before OD determination (and the plotted OD value then is corrected for the dilution). Two independent experiments were performed for each strain, and the growth curves were plotted as average OD$_{750}$ values over time in LL. For microarray and Northern blotting analyses, *Synechococcus* cells were grown in BG11 media in a continuous culture system (optical density of around 0.25 at 730 nm) at 30° C. and 40 μE/m$^2$ s. To synchronize the circadian clock, the culture was acclimated to 2 LD cycles and then transferred to LL in the presence or absence of 1 mM IPTG applied at LL24.

Microarray analysis. Total RNA was purified with the modified acid-hot phenol method. Iwasaki et al., Cell 101, 223-233 (2000). From total RNA samples, 1.5 μg of cDNA was prepared with a SuperScript III reverse transcriptase (Invitrogen) using random hexamers as primers (Invitrogen), partially fragmented with DNaseI (Takara) and biotylated by using an ENZO BioArray Terminal Labeling kit (ENZO Life Sciences). The labeled cDNAs were hybridized to the GeneChip arrays. The arrays were hybridized, washed, and stained by using standard Affymetrix prokaryotic GeneChip reagents and protocols. Affymetrix Gene Chip software was used to determine the average difference between matched mismatched oligonucleotide probes for each probe set. For better estimation of relative expression levels among different genes, we standardized each cDNA-derived signal with the corresponding genomic DNA-derived signal. We also performed hybridization of the *Synechococcus* oligonucleotide arrays with biotin-labeled DNaseI-fragmented genomic DNA.

The genomic DNA-derived signals varied within a range of 10-fold, whereas the RNA-derived signals (wild-type RNA samples collected at LL 12 as example) varied within a range of 10$^3$-fold. The signals for genomic DNA were within a linear range. Genomic DNA signals were scaled so that their average level was 1. Each RNA signal was then divided by the corresponding scaled genomic DNA signal. Values of RNA signals given hereafter indicate these genomic-DNA-normalized values. Ito et al., Proc. Natl. Acad. Sci. USA 106, 14168-14173 (2009). The raw data have been deposited in the National Center for Biotechnology Information's Gene Expression Omnibus database with an accession number GSE47015). Additionally, global normalization was applied to the RNA signal profiles under LL conditions so that the averages of the expression levels for all ORFs within a microarray were equal across arrays.

For normalization of microarray profiles presented in FIG. 1A, the averages and the standard deviations of the time-course profiles (LL 30-48, -IPTG) for each gene were initially calculated, and then the average values were subtracted from the signal at each indicated time, so that the time-course average level is 0. Finally, the edited signal values were divided by the standard deviation to normalize the resulting SD to 1.

Northern blots. Cells were harvested and immediately stored at −80° C. until RNA extraction. RNA was extracted from each sample as described above, and then subjected to electrophoresis, blotted onto nylon membranes, and hybridized with digoxigenin-labeled probes as described previously. Ishiura et al., Science 281, 1519-1523 (1998).

Quantitative real-time PCR (qRT-PCR). Total RNA was extracted by the hot phenol method with some modifications. Mohamed, A., and Jansson, C. Plant Mol. Biol. 13, 693-700 (1989) The cells collected from 30 ml cultures were treated with 1 ml Trizol, and incubated in a 65° C. water bath for 5 min. 0.2 ml chloroform was added per ml of Trizol and incubated in the 65° C. water bath for another 15 min, shaking from time to time to facilitate lysis. The subsequent phase extraction was done according to the Trizol extraction method. The extracted RNA was treated with the TURBO DNA free TM kit (Ambion) twice according to the instruction manual. About 1000 ng RNA was reverse-transcribed using the Agilent AffinityScript qPCR cDNA synthesis kit. The kaiA and kaiBC transcript levels were determined by quantitative RT-PCR. The housekeeping gene rnpB was chosen as an internal control gene to measure the relative levels of mRNA of target genes in vivo. Primer sequences are as follows: rnpB, f5'-GAAACATACCGCCGATGG-3' (SEQ ID NO: 6) and r5'-GTTGCTGGTGCGCTCTTAC-3' (SEQ ID NO: 7); kaiA, f5'-TCGCGACAGTGAGGATCCCGA-3' (SEQ ID NO: 8) and r5'-GTCTCGACCGGGGCTAAGCG-3' (SEQ ID NO: 9); kaiBC, f5'-GGAATATCCGTTCACGATTACG-3' (SEQ ID NO: 10) and r5'-GACGATCGCTGCGTAAGG-3' (SEQ ID NO: 11). Primer efficiency was determined using a standard curve for all the primers listed. All qRT-PCRs were carried out using an Applied Biosystems 73000 Real-time RCR system with SYBR green as fluorescent dye, and the specificity of each primer pair was tested by a melting curve analysis. Three experimental replications were performed and the raw data were processed using System 7300 Sequence Detection Software.

Immunoblotting for protein abundance. Cyanobacterial cells were harvested at the indicated time points. Total proteins were extracted as previously described (Xu et al., EMBO J. 19, 3349-3357 (2000)) and separated by SDS-polyacrylamide gel electrophoresis (PAGE) (15% for KaiA, KaiB, and GST-HPI; 10% for KaiC, Lux, and HyaB assays) and transferred onto nitrocellulose membranes. Gels were either stained with Coomassie Brilliant Blue (CBB) or transferred to nitrocellulose for immunoblotting using polyclonal rabbit antisera (raised against KaiA or KaiB or *Thiocapsa roseopersicina* HynL), monoclonal mouse antisera (raised against KaiC), polyclonal rabbit antisera against bacterial luciferase, or an affinity chromatography-purified GST epitope tag antibody (originally from polyclonal rabbit antisera, Novus, Littleton, Colo.). The immunoblots were analyzed with NIH Image J software.

Hydrogenase activity assays. In vitro hydrogen evolution assays were performed using cyanobacterial cell extracts, as described previously (Maroti et al., Appl. Environ. Microbiol. 75, 5821-5830 (2009)) with the following modifications. Cells (500 ml) were grown with constant air sparging and stirring at 28° C. under cool white fluorescence (30 µE $m^{-2} s^{-1}$). After indicated treatments, cells were centrifuged, resuspended in 1 ml sonication buffer (10 mM Tris-HCl, pH 7, 0.5 mM EDTA, 1 mM DTT), and sonicated under aerobic conditions twice for 2 minutes each on ice before being used for assays. The cell debris were removed by centrifugation, and the supernatants were used for hydrogenase activity assays. Hydrogenase assays were performed in 13.5 mL serum vials containing a total reaction volume of 2 mL consisting of 25 mM potassium phosphate, pH 7.0, 2 mM methyl viologen, and cell extract (approximately 20 µg total protein). The assay vials were capped with rubber septa and sparged with argon gas to remove oxygen, and 100 µl of 2M sodium dithionite pH 7.0 was added to begin the reaction. Reactions were incubated at 30° C., and at various time points 100 µl of headspace gases including hydrogen were analyzed by gas chromatography (CP-3800, Varian) using a Fused Silica Molsieve 5A column (CP7537, Varian).

Student's t-test and R-squared were performed for statistical analyses.

Results

KaiA-OX Enhances Expression of Subjective Dusk Genes: Microarray Analyses

In vivo overexpression of kaiC has been claimed to globally repress gene expression in *S. elongatus* (Nakahira et al., Proc. Natl. Acad. Sci. USA 101, 881-885 (2004)), but the converse manipulation of pervasively enhancing gene expression by manipulation of the clock has not been studied. Since the KaiABC-based oscillator globally regulates gene expression in cyanobacteria and kaiA-OX enhances the expression of the kaiBC promoter (Ishiura et al., Science 281, 1519-1523 (1998)), we reasoned that KaiA could be enlisted to act as a positive regulator to enhance expression on a genomic scale. Using a luciferase reporter of the expression of the Class I photosynthetic gene psbAI (psbAIp::luxAB), we found that the response of the psbAI promoter to overexpression of kaiA (kaiA-OX) is both acute and sensitive (See FIG. 1A-1C). When kaiA expression was stimulated with the inducer isopropyl β-D-1-thiogalactopyranoside (IPTG), psbAIp::luxAB expression quickly increased to a high level that was essentially arrhythmic (FIG. 1B), and this response to kaiA-OX was dependent on IPTG dose; concentrations of IPTG as low as 15-20 µM eliminated the clock-controlled luminescence rhythm (FIG. 1C). The addition of IPTG to cells that do not harbor an IPTG-derepressible promoter (i.e., trcp) does not elicit any changes in gene expression. Moreover, overexpression of kaiA had no marked effect on the growth rates among different reporter strains in constant light, aka LL (FIG. 1D).

To evaluate KaiA's genome-wide regulation, we performed microarray assays in the kaiA-overexpressing strains with or without IPTG induction (FIG. 2A). The expression profile of each clock-controlled gene in kaiA-OX cells with IPTG induction in constant light (LL) from 30 to 48 h was compared with that in the absence of IPTG (LL30-48) (FIG. 2A). In response to kaiA-OX, about 20% of the genes were up-regulated and about 12% were down-regulated, with the remaining ~68% of genes not clearly affected by kaiA-OX. In comparison with the genes that are repressed vs. enhanced by overexpression of kaiC (kaiC-OX), there is a clear trend that kaiA-OX and kaiC-OX have opposite effects for most genes (FIG. 2B; FIGS. 3A and 3B). Among 800 cycling genes revealed by microarrays, kaiA-OX mostly up-regulates "subjective dusk" genes (expression mostly in the daytime, with peak expression at Circadian Time 12 {CT12}≈36 h in LL, aka Class I genes) and down-regulates "subjective dawn" genes (peak expression at CT0≈24 & 48 h in LL, aka Class II genes, FIG. 2C-2E), whereas kaiC-OX was shown to repress dusk genes and activate dawn genes. Ito et al., Proc. Natl. Acad. Sci. USA 106, 14168-14173 (2009).

Figure 4:
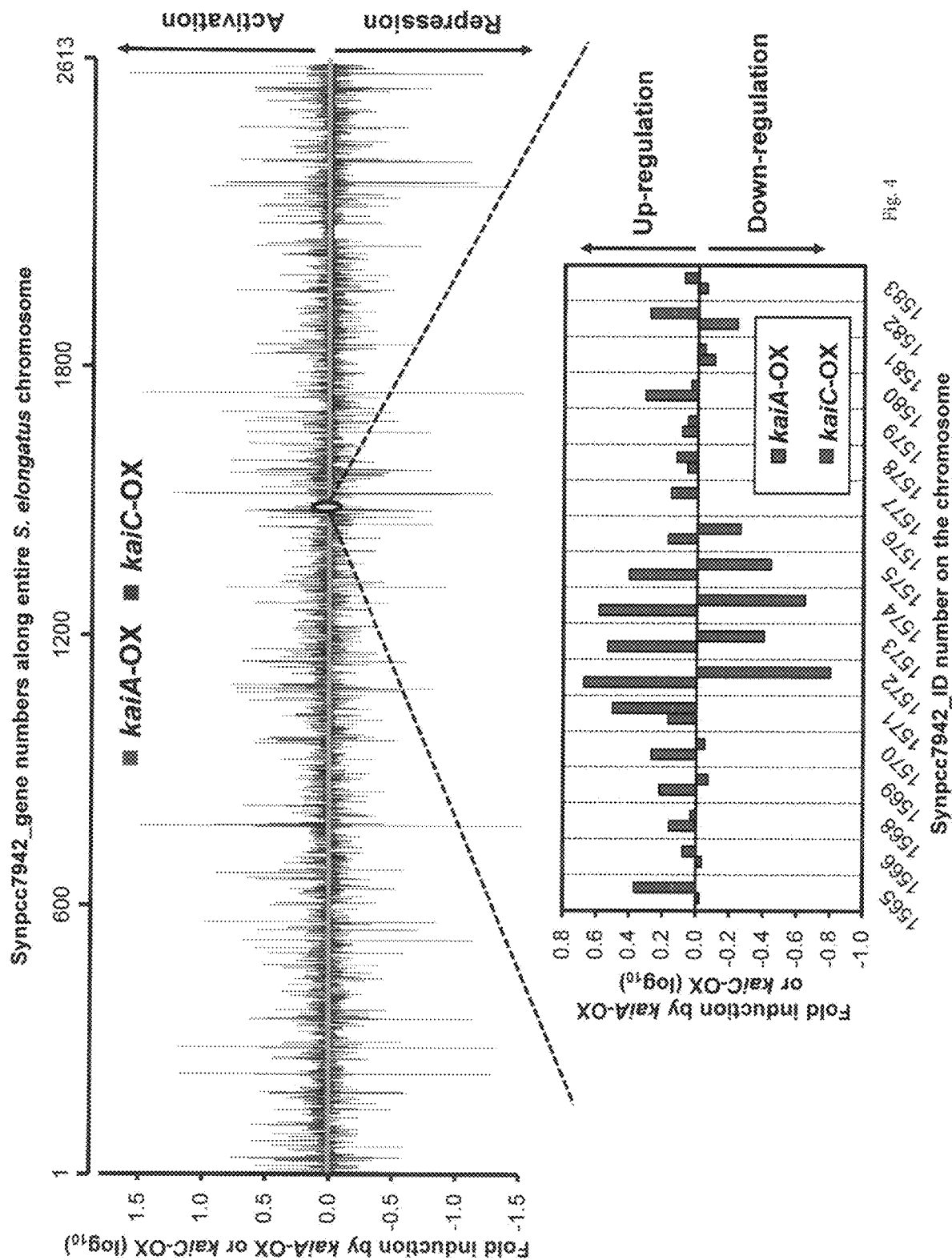
FIG. 4 provides a graph showing the spatial patterns of gene expression along the entire S. elongatus chromosome elicited by kaiA/kaiC overexpression. The S. elongatus chromosome is circular, but it is here shown in linear format with the expression levels of each gene in response to kaiA-OX or kaiC-OX. Changes of gene expression are shown as the ratio of the transcript abundance in the presence of IPTG to that in the absence of IPTG in LL. Each ratio was arranged in ascending order of Synpcc7942 gene number (i.e., "1200" means gene "Synpcc7942_1200"). The lower panel magnifies the region encompassing Synpcc7942_1565 to Synpcc7942_1583 where changes expression levels regulated by kaiA-OX and kaiC-OX are denoted. Increased gene expression in response to the indicated overexpression is classified as up-regulation (activation), whereas decreased transcript levels are considered down-regulation (repression).

Although there may be some positional effects of these opposing regulatory patterns based on rhythmic changes in chromosomal topology, there is not an obvious clustering pattern along the chromosome of the genes that are up-regulated vs. down-regulated by kaiA-OX (FIG. 3C; FIG. 4). On the other hand, there is an obvious correlation of genes along the chromosome that are up-regulated by kaiA-OX with those that are inversely down-regulated by kaiC-OX, and vice-versa (FIG. 4), as confirmed by the statistically significant regression shown in FIG. 2B ($R^2$=0.683). Therefore, kaiA-OX vs. kaiC-OX complementarily regulate circadian expression patterns. As will be shown below, continuous overexpression of kaiA locks the expression of these output genes at constitutively high or low levels and arrests rhythmic expression by the constitutive hyperphosphorylation of KaiC. Iwasaki et al., Proc. Natl. Acad. Sci. USA 99, 15788-15793 (2002).

Figures 5A, 5B:
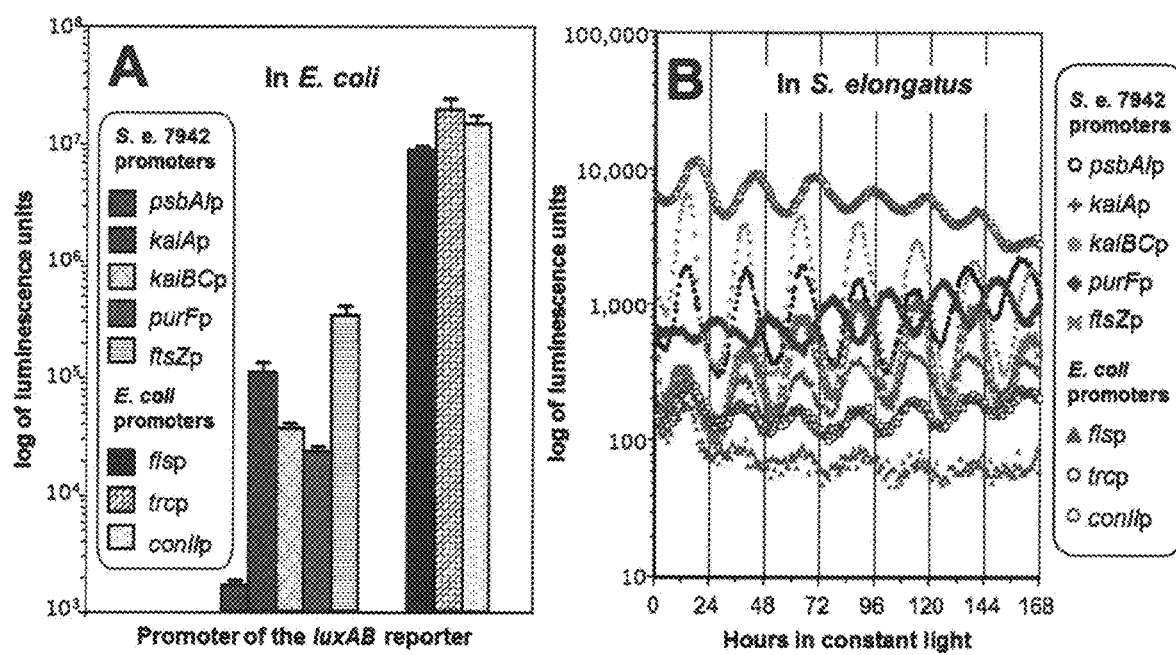
FIGS. 5A and 5B provide graphs showing the expression of various promoter::luxAB reporter constructs in E. coli and S. elongatus. (A) Expression of luxAB luminescence reporters of various promoters in E. coli. Luminescence was measured from 0.5 ml of cells at a concentration adjusted to OD=0.5 from E. coli cultures grown overnight. (B) Rhythmicity profiles of luxAB reporters driven by diverse promoters in cyanobacteria. Following a 12 h dark treatment, luminescence rhythms were monitored in LL in cultures of uniform cell density (30 at $OD_{750}$=0.3) placed on agar medium for the different promoter::reporter strains. Corresponding promoters are as indicated. Note that the ordinal values are shown on a $log_{in}$ scale in arbitrary units of luminescence. "S.e. 7942" denotes S. elongatus PCC 7942.

Effect of kaiA-OX on Gene Expression at "Neutral Sites" Using Luminescence Reporters To monitor in real-time the effect of KaiA on promoter activities, we examined luminescence reporters driven by the promoters of diverse S. elongatus genes, including the central clock genes (kaiA and kaiBC), the photosynthesis gene psbAI, the purine biosynthesis pathway gene purF, and the cell division gene ftsZ. These genes exemplify both expression patterns: kaiAp, kaiBCp, psbAIp, and ftsZp are Class I promoters, while purFp is a Class II promoter. We also examined heterologous E. coli promoters that are recognized by the transcriptional apparatus of S. elongatus, such as those from the f is factor for site-specific DNA inversion (a marker of local DNA topology (Gille et al., Nucleic Acids Res. 19, 4167-4172 (1991)), an IPTG-derepressible heterologous promoter trc (Xu et al., EMBO J. 22, 2117-2126 (2003)), and the σ70 binding site gene conII (Elledge, Proc. Natl. Acad. Sci. USA 86, 3689-3693 (1989)), all of which are expressed in the Class I (dusk) phase in S. elongatus (FIG. 5B). Although all of these reporters were expressed in both E. coli and S. elongatus, their expression levels were quite different between these two bacteria. While reporters driven by cyanobacterial promoters express at much lower levels in E. coli than those from E. coli (a phenomenon that is particularly noticeable in the case of the psbAI promoter; FIG. 5A), in S. elongatus the E. coli reporters exhibited both the strongest (e.g. conIIp::luxAB) and the weakest expression (e.g. fisp::luxAB; FIG. 5B). Nevertheless, all of the reporters-independent of the source of the promoter—were rhythmic in cyanobacteria (FIG. 5B), a phenomenon that is likely due to circadian control over chromosomal topology in S. elongatus that modulates promoter activity globally. Woelfle et al., Proc. Natl. Acad. Sci. USA 104, 18819-18824 (2007). We then integrated an IPTG-inducible expression cassette of wild-type kaiA with a 5'-untranslated sequence (trcp::kaiA) into either neutral site I or neutral site II of these reporter strains to examine the impact of kaiA-OX on the activity of these various promoters. Overexpression of kaiA constantly enhanced the promoter activities of the central clock genes (kaiAp and kaiBCp) when IPTG was applied to cells at either the beginning of LL treatment (LL0) or 48 h later (LL48), whereas kaiBC-OX repressed kaiBCp activity (FIG. 6A; FIGS. 7A and 7B).

Moreover, kaiA-OX increased the levels of kaiBC and luxAB transcripts when IPTG was added at LL24 (FIG. 6B; FIGS. 7C and 7D). Increased KaiA also enhanced the abundance of the KaiB and KaiC proteins, and promoted the hyperphosphorylation of KaiC (FIG. 6C), which is consistent with KaiA's ability to stimulate KaiC phosphorylation in vitro and in vivo, and inhibit dephosphorylation. To obtain even stronger production of KaiA, in some of our experiments we used an IPTG-derepressible trcp::kaiA fusion gene with an ATG start codon, i.e. trcp:: {ATG}kaiA (rather than the aforementioned construct with a GTG start codon) (FIGS. 7E and 7F). In contrast to the consequences of kaiA-OX, kaiC-OX floods the system with newly synthesized KaiC, which reduces the overall phosphorylation status of the KaiC pool. Therefore, kaiA-OX and kaiC-OX have complementary effects on the status of KaiC phosphorylation and therefore mimic opposite points of the endogenous oscillation of KaiC phosphorylation that are 180° out of phase (see FIG. 12A).

Figure 9B:
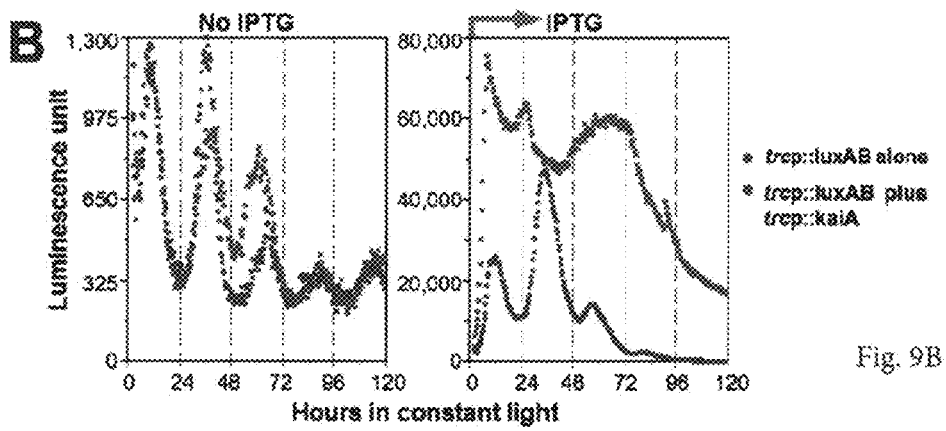

An indicator of the global, non-discriminatory control of the S. elongatus genome by the KaiABC-based clock is whether heterologous promoters/genes can be controlled in a similar fashion to endogenous promoters/genes. To determine if kaiA-OX can enhance expression of foreign gene promoters, we tested strains expressing luxAB under the control of conIIp-a strong promoter that is "constitutively" expressed in E. coli. Luminescence activities controlled by conIIp exhibited high levels of rhythmic expression in S. elongatus, and kaiA-OX further enhanced this strong promoter's activity up to ~3.5 fold higher than that of controls without kaiA induction (FIGS. 6D & 6E). This kaiA-OX mediated enhancement of luminescence activity under the control of conIIp appears to occur by boosting the trough levels of the conIIp::luxAB expression profile to be at or above the peak levels (FIG. 6D). KaiA also positively regulates a usefully inducible, non-cyanobacterial promoter, trcp. KaiA-mediated enhancement of luminescence expression is particularly dramatic in a S. elongatus strain co-expressing both IPTG-inducible constructs (trcp::luxAB reporter and trcp::kaiA) (FIG. 9A). In the absence of IPTG induction, the artificial promoter trc could drive circadian luminescence oscillations at low levels in both the reporter strain (trcp::luxAB) and the reporter/kaiA-coexpressing strain (trcp::luxAB+trcp::kaiA; FIG. 6F; FIG. 9B). In the presence of IPTG, overall promoter activity was increased in the trcp::luxAB reporter strain but the pattern remained rhythmic (FIG. 6F), whereas in the strain co-expressing the trcp::luxAB reporter and trcp::kaiA, kaiA overexpression further stimulated the activity of the strong trc promoter but the rhythmic pattern was lost (FIGS. 6F & 6G). Therefore, kaiA-OX not only enhances the expression of diverse cyanobacterial "subjective dusk" Class I genes in situ (FIG. 2), it also stimulates the activity of cyanobacterial kai promoters and of the strong E. coli promoters conIIp and the IPTG-depressible promoter trcp when placed into neutral sites NSI or NSII (FIG. 6).

Enhancing Expression of Endogenous Hydrogenase Genes by kaiA-OX

The quest to understand the role of KaiA in regulating KaiC phosphorylation status and therefore gene activity led to the recognition that expression of subjective dusk genes (the predominant Class I genes) could be constitutively enhanced by this rewiring of the circadian circuitry. Thereby, enhanced production of useful bioproducts, such as biofuel compounds encoded by foreign and/or endogenous genes, could be accomplished by kaiA-OX. Hydrogen ($H_2$) is an attractive carbon-free energy storage molecule, and production of $H_2$ using photosynthetic cyanobacteria could provide an alternative to fossil fuels by using solar energy to convert $H_2O$ into hydrogen. Hydrogenases catalyze the reversible reduction of protons to $H_2$ and can be divided into three phylogenetically-distinct categories that correlate with the metal composition of the active site: [FeFe], [NiFe], and

[Fe]-cluster-free hydrogenases. *S. elongatus* has one native [NiFe] hydrogenase. Interestingly, our microarray analysis revealed that kaiA-OX promoted mRNA profiles of all NAD-reducing hydrogenase subunits (FIG. 8A). Therefore, we first examined the impact of kaiA-OX (trcp::{ATG}kaiA) upon the expression of endogenous [NiFe] hydrogenase in *S. elongatus*. As shown in FIG. 8B, endogenous [NiFe] hydrogenase activities were enhanced in the kaiA-OX strain in constant light even without IPTG induction due to "leaky" expression of KaiA in the trcp::{ATG}kaiA strain. Mild induction of KaiA with 20 μM of IPTG further boosted hydrogenase activity. Overexpression of KaiA also caused consistently high levels of hydrogenase activity in a LL time course experiment in the kaiA-OX strain (+20 μM IPTG) relative to wild-type strain (FIG. 8C).

kaiA-OX-Enhanced Production of Foreign Proteins in LD, LL, and DD

The kaiA-OX strategy can also be used to enhance the expression of heterologous genes, resulting in the accumulation of foreign proteins. Bacterial luciferase is an example of a foreign protein that is expressed well in *S. elongatus* as a reporter of promoter activity (e.g., FIG. 6). Moreover, our kaiA-OX strategy up-regulates the accumulation of LuxAB protein very significantly (nearly 7-fold in the experiment depicted in FIGS. 10A & 10B). As indicated above, hydrogenase is a protein of biotechnological interest, but because photosynthesis generates oxygen, production-scale generation of $H_2$ by photosynthetic microbes will ultimately require exogenous hydrogenases that are more tolerant of oxygen. While [FeFe] and [Fe]-hydrogenases are rapidly inactivated by oxygen, [NiFe]-hydrogenases are more active in the presence of photosynthetically produced oxygen. Fritsch et al., Nature Rev. Microbiol. 11, 106-114 (2013). Recently, heterologous expression of a [NiFe]-hydrogenase from *Alteromonas macleodii* Deep Ecotype with tolerance to partial oxygen was demonstrated in *S. elongatus*, generating a strain called RC41. Weyman et al., PLoS ONE 6, e20126 (2011). RC41 features a knockout of the endogenous hoxYH genes encoding the bidirectional [NiFe] hydrogenase (HoxYH), and the trcp-driven expression cluster encoding the *A. macleodii* [NiFe] hydrogenase HynSL and other 11 surrounding accessory proteins were expressed from the NS I site under the control of trcp as shown in FIG. 11A. Generally, two subunits (ca. 60 kDa and 30 kDa) are involved in the catalytic core of [NiFe] hydrogenases, and the larger subunit contains the [NiFe] catalytic site that requires an extensive set of accessory proteins to assemble an active catalytic site. Bock et al., Adv. Microb. Physiol. 51, 1-71 (2006). While the RC41 strain achieves some hydrogenase activity, low expression of the multiple hydrogenase & accessory protein genes was problematic.

To test if KaiA can stimulate the expression of the foreign [NiFe] hydrogenase from *A. macleodii* in *S. elongatus*, we introduced the trcp::{ATG}kaiA construct into the NS II site of the RC41 strain and examined the abundance of the large subunit, HynL, as a marker for expression of the foreign *A. macleodii* hydrogenase cassette. We found that neither deletion of endogenous hoxYH genes nor overexpression of *A. macleodii* hydrogenase cluster genes affected the period or phase of the clock in *S. elongates* (FIG. 11B). When kaiA was additionally expressed in the RC41 strain (+20 μM of IPTG), the abundance of the foreign *A. macleodii* hydrogenase large subunit, HynL, significantly increased relative to a control strain without the trcp::{ATG}kaiA expression cassette (FIGS. 10C & 10D). Immunoblot assays confirmed that kaiA-OX also enhanced KaiC protein levels in the hoxYH-null mutant strain co-expressing *A. macleodii* hydrogenase cluster genes and trcp::{ATG}kaiA (FIG. 10C; FIG. 11C). Compared to the native hydrogenase activity in wild-type *S. elongatus*, the activity of the foreign *A. macleodii* hydrogenase in the RC41 strain is lower (FIG. 10E), and therefore methods to further enhance activity would be necessary before this strategy could be useful industrially. We conjecture that part of the difficulty could be that this hydrogenase operon is so large (about 13 kb) that not all of the genes are expressed well. Additionally, there may be post-transcriptional constraints to overcome so as to achieve higher hydrogenase activity in vivo in *S. elongatus*. Nevertheless, overexpression of kaiA increased approximately twofold the activity of $H_2$ production from the foreign [NiFe] hydrogenase as well as HynL abundance in the RC41 strain (FIG. 10C-10E).

As an another example illustrating how manipulation of kaiA expression can enhance production of foreign proteins in cyanobacteria, we generated a GST::HPI/KaiA strain, in which a fusion protein between the foreign gene encoding human proinsulin (HPI) and the glutathione S-transferase (GST) tag was expressed under the control of the non-cyanobacterial promoter conIIp in NS I, and the expression cassette trcp::{ATG}kaiA was cloned into NS II (FIG. 11D). Under both light:dark (LD) and LL conditions, kaiA-OX increased production of the foreign GST::HPI fusion protein (FIGS. 10F & 10G; FIGS. 11E and 11F). We noticed that the accumulation of GST::HPI was particularly high in the dark portion of LD (FIGS. 10F & 10G), so we tested the expression under constant darkness (DD) and found that kaiA-OX significantly enhanced the accumulation of GST::HPI in extended darkness (FIGS. 10H & 10I), which was unexpected given that *S. elongatus* is an obligate photoautotroph.

DISCUSSION

The circadian rhythm of KaiC phosphorylation regulates the global patterns of gene expression in *S. elongatus*. The peak and trough levels of the KaiC phosphorylation rhythm can be mimicked by overexpression of KaiA or KaiC, respectively (FIG. 12A). Therefore, the opposing actions of kaiA-OX vs. kaiC-OX form a "Yin-Yang" action, by analogy to the Taoist concept of inverse forces that complementarily interact to form a greater whole (FIGS. 12A & 12B). Increased KaiA levels stimulate KaiC phosphorylation and inhibits KaiC dephosphorylation, thereby promoting KaiC hyperphosphorylation and expression of dusk (Class I) genes (FIG. 12B). In the usual post-translational oscillator (PTO) cycle, hyperphosphorylated KaiC interacts with KaiB to form a KaiA/KaiB/KaiC complex that allows KaiC to dephosphorylate, and this process can be induced by kaiC-OX, which disturbs the normal stoichiometry of Kai A:B:C proteins. The phosphorylation status of the PTO then regulates transcriptional endpoints by output pathways that include SasA, CikA, LabA, RpaA, and RpaB. Taniguchi et al., Proc. Natl. Acad. Sci. USA 107, 3263-3268 (2010). Therefore, kaiA-OX vs. kaiC-OX inversely switch the KaiC phosphorylation status and gene expression patterns between dusk (kaiA-OX) and dawn (kaiC-OX) phases (FIGS. 12A & 12B). In addition, constant induction of KaiA or KaiC both lead to arhythmic expression patterns (FIG. 12A).

Our experimental observations led us to re-evaluate the claim that the "negative element" KaiC is a global repressor of gene expression. In fact, microarray analyses of the impact of kaiC-OX on gene expression in *S. elongatus* in conjunction with our examination of kaiA-OX herein reveal that BOTH KaiA and KaiC can repress AND enhance transcript abundances, and that they appear to have opposite effects on the expression of many genes (FIGS. 2 & 4; FIGS. 3A and 3B). Why then did it appear that KaiC is a global repressor of promoter activities? Nakahira et al., Proc. Natl. Acad. Sci. USA 101, 881-885 (2004). That conclusion was based upon the insertion of many different randomly chosen promoters into neutral site I (NSI). That particular site in the S. elongatus genome (position 2578661) is downregulated by kaiC-OX and up-regulated by kaiA-OX (FIG. 3C). We suggest that the neutral site chosen for the random promoter analysis is topologically regulated by the circadian system so that any promoter placed in that site is repressed by KaiC and enhanced by KaiA as a Class I gene independently of how the promoter is regulated in situ.

We exploit these insights into the fundamental regulation of gene expression in S. elongatus to propose a strategy for maximizing the expression of genes that encode industrially useful products, where non-rhythmically "latching" production at the peak level would be optimal. In this investigation, we report that overexpression of kaiA up-regulates many endogenous genes in situ as well as foreign genes expressed from NS I and NS II. Moreover, kaiA-OX attenuates the circadian rhythm, so that latching of expression at the circadian peak level for many genes is achievable. Surprisingly, this reprogramming of circadian expression patterns does not appear to have significant impact upon growth rates of S. elongatus in constant light. Therefore, enhanced accumulation of a useful product would be expected with kaiA-OX (compare the blue cross-hatched area with the pink area in FIG. 12C).

In addition to the impact of kaiA-OX on expression levels of foreign genes expressed from NS I or NS II, the suppression of the circadian rhythm by kaiA-OX can also be advantageous if production of bioindustrial molecules or other gene products is conducted over a grueling 24 h/day, 7 days/week schedule (i.e., "24/7") under constant illumination. Consistent expression over 24 h with cells maintained in LL opens the possibility of creating bioproduct in both the day phase and the night phase (S. elongatus cells are normally quiescent in the night phase), thereby boosting yield (FIG. 12C). The data of FIG. 10E-10I also suggest that the expression of some foreign proteins may be stronger in the dark in combination with kaiA-OX. Because the transcription & translation of most endogenous genes is shut down during the dark in S. elongates (Tomita, et al., Science 307, 251-254 (2005)), this may allow the new synthesis that occurs in darkness to be preferentially weighted to that of foreign genes of industrial interest. We show here the application of stimulating the production of biofuel- and pharmaceutical-related proteins, but this tactic can be potentially used to increase expression of any protein or pathway of industrial importance. Moreover, the overall principle of inactivating the circadian system so that it latches at the peak expression is not restricted to cyanobacteria, but may be useful for 24/7 industrial applications with any organism that has a circadian clock, including eukaryotic organisms where the circadian system regulates 10-20% of the genome (e.g., transgenic expression in plants as "bioreactors").

Example 2

Figure 13A:
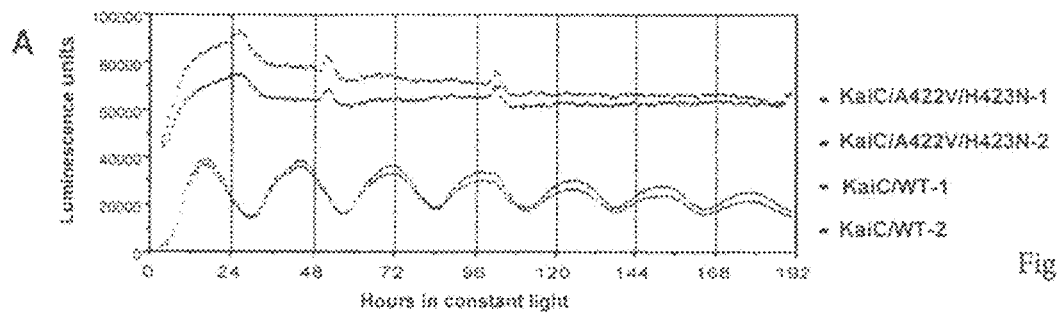
FIGS. 13A-13C provide graphs showing that manipulation of mutant variants of the negative component KaiC also constantly enhances gene expression. A. Comparison of psbAIp::luxAB rhythmicity and expression levels between wild-type KaiC strain (KaiC/WT) and double mutant KaiC strain (KaiC/A422V/H423N) in constant light without any special treatment (such as an inducer like IPTG). Two replicate examples are shown for each strain. B. The expression patterns of the psbAIp::luxAB reporter in the wild-type strain (WT) alone and in overexpressing strains with different versions of KaiC under the control of the IPTG-inducible trc promoter (KaiC/WT-OX=trcp::wild-type kaiC; KaiBC/WT-OX=trcp::wild-type kaiB & kaiC; KaiC/EE-OX=trcp::double mutant kaiC/S431E-T432E. In constant light (LL), when IPTG was applied at hour LL24, overexpression of either wild-type KaiC or KaiB & KaiC constantly represses the reporter expression, whereas overexpression of the double mutant KaiC/EE continuously boosts the luminescence expression. C. Overexpression of the double mutant KaiC/EE constantly enhances abundance of the foreign luciferase protein. Top panel shows immunoblots of *Vibrio harveyi* luciferase protein (LuxA) in the psbAIp::luxAB-expressing wild-type strain (WT) and a KaiC-manipulated strain with trcp::KaiC/EE (WT/KaiC-EE/OX) in constant light with or without 0.1 mM IPTG. The luciferase protein signal is indicated by "LuxA," and a constitutive nonspecific band is marked "nb." Bottom panel is the densitometry of the *V. harveyi* LuxA abundance from the immunoblots above, which was calculated from the ratio of LuxA:nb abundance.
Figure 13B:
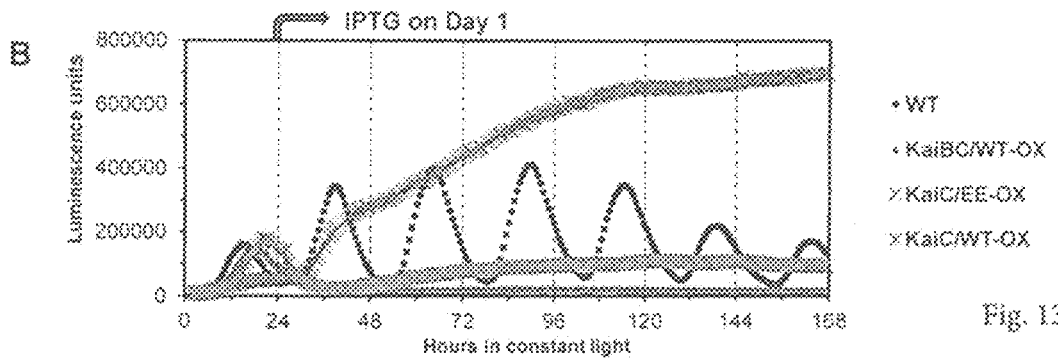
Figure 13C:
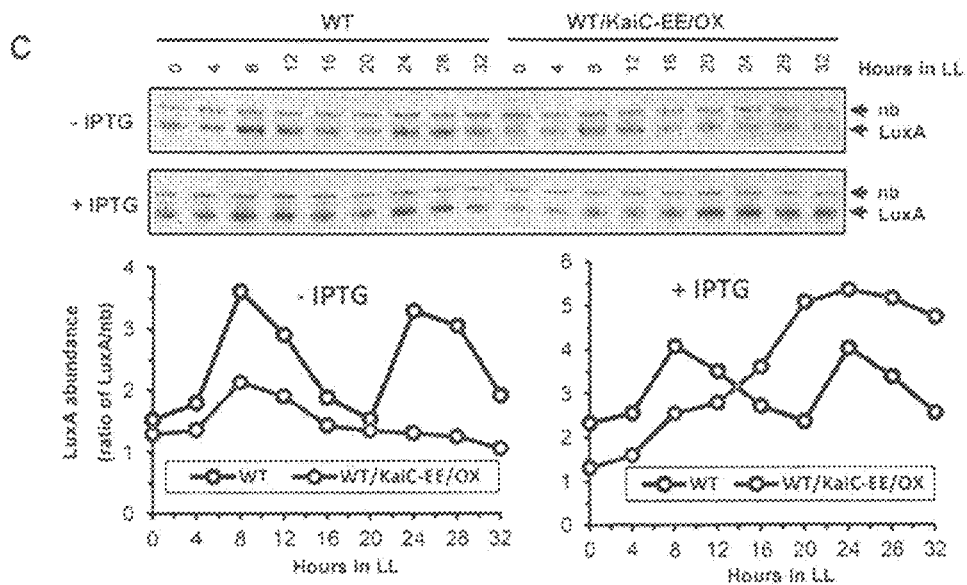
Figures 14A, 14B:
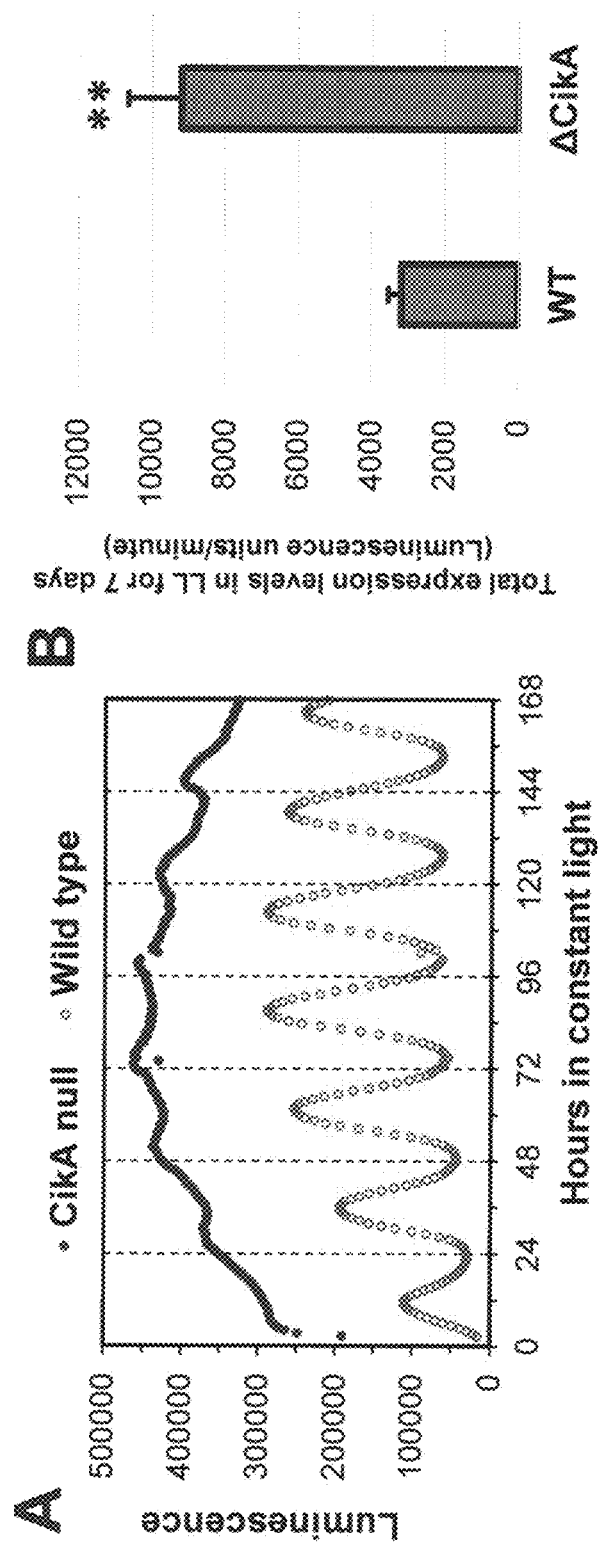
FIGS. 14A and 14B provides graphs showing that constant high expression of the reporter gene in a strain in which an input pathway component of the circadian system (cikA) has been genetically knocked out (A or null strain). In this case, no treatment with an inducer (such as IPTG) is necessary to achieve high output gene expression. A. Luminescence expression profiles of the wild-type strain (WT) and cikA-null strain (CikA null) in constant conditions. B. Total expression levels in constant light for 7 days were calculated as luminescence units per minute in wild-type strain (WT) and cikA-knockout strain (ΔCikA). **$p<0.001$.

Further Studies of Circadian Regulation Involving a Double KaiC Mutation and ΔCikA Knockout Additional work was carried out to demonstration the effect of mutation of clock genes or clock-related genes on gene expression. FIG. 13 shows that in addition to overexpression of the positive clock component KaiA, manipulation of mutant versions of the negative component KaiC also constantly enhances gene expression (in this case, the mutant versions KaiC/A422V/H423N (SEQ ID NO: 12) and KaiC/EE (SEQ ID NO: 13)). Besides experimental manipulation of central clock genes such as KaiA and KaiC, FIG. 14 illustrates that manipulation of other clock-related genes can result in constant high expression of reporter gene even without any induction or special treatment. In this particular example, it is the deletion of an input pathway gene of the circadian system, called cikA (SEQ ID NO: 14), that results in constant high expression of the output gene.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of increasing gene expression, comprising transforming a cyanobacteria with (a) a first construct comprising a first promoter and a clock gene, wherein the first promoter results in overexpression of the clock gene to which the first promoter is operably linked, and (b) a second construct comprising a second promoter and a target gene to which the second promoter is operably linked, thereby resulting in a change to the circadian cycle of the cyanobacteria that increases expression of a target gene expressing a protein or a biofuel product or precursor, wherein the second promoter is regulated by a clock signal-transmitting gene, and wherein the clock gene is selected from SEQ ID NO: 3, SEQ ID NO: 4, and SEQ ID NO: 5, wherein the target gene is not luciferase and wherein the clock signal-transmitting gene is selected from the group consisting of SasA, CikA, LabA, RpaA and RpaB.

2. The method of claim 1, wherein the cyanobacteria is *Synechococcus elongatus*.

3. The method of claim 1, wherein the clock gene is SEQ ID NO: 3 or SEQ ID NO: 5.

4. The method of claim 1, wherein overexpression of the clock gene suppresses the circadian rhythm of the cyanobacteria.

5. The method of claim 1, wherein the target gene is a biofuel product or biofuel precursor expressing gene.

6. The method of claim 1, wherein the target gene is a heterologous gene.

7. The method of claim 6, wherein the heterologous gene is a hydrogenase expressing gene.

8. The method of claim 6, wherein the heterologous gene is a pro-insulin expressing gene.

9. A cyanobacteria, comprising a cyanobacteria that has been transformed to comprise (a) a first construct comprising a first promoter wherein the first promoter results in the overexpression of the clock gene to which the first promoter is operably linked, and (b) a second construct comprising a second promoter and a target gene to which the second promoter is operably linked, thereby resulting in a change to the circadian cycle of the cyanobacteria that increases expression of a target gene expressing a protein or a biofuel product or precursor, wherein the second promoter is regulated by a clock signal-transmitting gene, and, wherein the clock gene is selected from SEQ ID NO: 3, SEQ ID NO: 4, and SEQ ID NO: 5, wherein the target gene is not luciferase and wherein the clock signal-transmitting gene is selected from the group consisting of SasA, CikA, LabA, RpaA and RpaB.

10. The cyanobacteria of claim 9, wherein overexpression of the clock gene suppresses the circadian rhythm of the cyanobacteria.

11. The cyanobacteria of claim 9, wherein the target gene is a gene influencing the expression of a biofuel product or biofuel precursor.

12. The cyanobacteria of claim 9, wherein the cyanobacteria is a transgenic cyanobacteria, and the target gene is a heterologous gene.

13. The cyanobacteria of claim 9, wherein the clock gene is SEQ ID NO: 3 or SEQ ID NO: 5.

* * * * *

UNITED STATES PATENT AND TRADEMARK OFFICE
CERTIFICATE OF CORRECTION

PATENT NO. : 10,927,365 B2
APPLICATION NO. : 14/933622
DATED : February 23, 2021
INVENTOR(S) : Carl Hirschie Johnson et al.

It is certified that error appears in the above-identified patent and that said Letters Patent is hereby corrected as shown below:

In the Specification

In Column 1, Lines 14-18, please delete the paragraph and insert:
--This invention was made with government support under Grant Nos. GM067152 and GM088595, awarded by the National Institutes of Health, and Contract No. DE-FG36-05G015027, awarded by U.S. Department of Energy. The government has certain rights in the invention.-- therefor.

Signed and Sealed this
Twenty-sixth Day of September, 2023

Katherine Kelly Vidal
*Director of the United States Patent and Trademark Office*

SEQUENCE LISTING

```
<160> NUMBER OF SEQ ID NOS: 14

<210> SEQ ID NO 1
<211> LENGTH: 5781
<212> TYPE: DNA
<213> ORGANISM: Artificial Sequence
<220> FEATURE:
<223> OTHER INFORMATION: Neutral Site 1 vector pAM1303

<400> SEQUENCE: 1
actcaccagt cacagaaaag catcttacgg atggcatgac agtaagagaa ttatgcagtg      60
ctgccataac catgagtgat aacactgcgg ccaacttact tctgacaacg atcggaggac     120
cgaaggagct aaccgctttt ttgcacaaca tgggggatca tgtaactcgc cttgatcgtt     180
gggaaccgga gctgaatgaa gccataccaa acgacgagcg tgacaccacg atgcctgcag     240
caatggcaac aacgttgcgc aaactattaa ctggcgaact acttactcta gcttcccggc     300
```

```
aacaattaat agactggatg gaggcggata aagttgcagg accacttctg cgctcggccc    360
ttccggctgg ctggtttatt gctgataaat ctggagccgg tgagcgtggg tctcgcggta    420
tcattgcagc actggggcca gatggtaagc cctcccgtat cgtagttatc tacacgacgg    480
ggagtcaggc aactatggat gaacgaaata gacagatcgc tgagataggt gcctcactga    540
ttaagcattg gtaactgtca gaccaagttt actcatatat actttagatt gatttaaaac    600
ttcattttta atttaaaagg atctaggtga agatcctttt tgataatctc atgaccaaaa    660
tcccttaacg tgagttttcg ttccactgag cgtcagaccc cgtagaaaag atcaaaggat    720
cttcttgaga tccttttttt ctgcgcgtaa tctgctgctt gcaaacaaaa aaaccaccgc    780
taccagcggt ggtttgtttg ccggatcaag agctaccaac tcттттттccg aaggtaactg    840 gcttcagcag agcgcagata ccaaatactg tccttctagt gtagccgtag ttaggccacc    900
acttcaagaa ctctgtagca ccgcctacat acctcgctct gctaatcctg ttaccagtgg    960
ctgctgccag tggcgataag tcgtgtctta ccgggttgga ctcaagacga tagttaccgg   1020
ataaggcgca gcggtcgggc tgaacggggg gttcgtgcac acagcccagc ttggagcgaa   1080
cgacctacac cgaactgaga tacctacagc gtgagctatg agaaagcgcc acgcttcccg   1140
aagggagaaa ggcggacagg tatccggtaa gcggcagggt cggaacagga gagcgcacga   1200
gggagcttcc agggggaaac gcctggtatc tttatagtcc tgtcgggttt cgccacctct   1260
gacttgagcg tcgatttttg tgatgctcgt caggggggcg gagcctatgg aaaaacgcca   1320
gcaacgcggc ctttttacgg ttcctggcct tttgctggcc ttttgctcac atgttctttc   1380
ctgcgttatc ccctgattct gtggataacc gtattaccgc ctttgagtga gctgataccg   1440
ctcgccgcag ccgaacgacc gagcgcagcg agtcagtgag cgaggaagcg gaagagcgcc   1500
tgatgcggta ttttctcctt acgcatctgt gcggtatttc acaccgcata tggtgcactc   1560
tcagtacaat ctgctctgat gccgcatagt taagccagta tacactccgc tatcgctacg   1620
tgactgggtc atggctgcgc cccgacaccc gccaacaccc gctgacgcgc cctgacgggc   1680
ttgtctgctc ccggcatccg cttacagaca agctgtgacc gtctccggga gctgcatgtg   1740
tcagaggttt tcaccgtcat caccgaaacg cgcgaggcag gatatccggc agccggcgga   1800
gcgctgcttt cttggcaagc ggtcgccagc cccaacgcca gggctgccag cccgaaacag   1860
cggggcaagg cagcttggaa gggcgatcgc agcacgggca tggcaatgtc tctctgaagg   1920
aatgcagacc ttattcgtac agccagggtt gaatcgtggg ggtccaatca cttagctctg   1980
ctgggctaaa ccagagagca atttcctgtt gtgctgtttc gattgcatcc gagccatgga   2040
tgatgttgcg gccaatattg acaccaaaat caccacggat ggtgcccggt tctgccgtca   2100
gcggattggt agcgccgatc aacttgcgag cagccgccac aacgccttcg ccttccaaga   2160
cgatcgccac gatcggccca gaggtgatga actcgacgag gccattgaag aagggcgct   2220 cgcggtggac agcatagtgc tgttcggcca gctcgcgact gggcttcagc tgctttaggc   2280
ccaccagttt gaagcctttt tgctcaaagc ggccgatgat cgtaccgacc aaacccgct   2340 gaacgccatc gggcttgatg gcaataaatg tgcgttccac agacatctag atagtcctca   2400
agacgaggca agcattgagc ttgccttcct atggttcggg atcactggga ttcttgacaa   2460
gcgatcgcgg tcacatcgct atctcttagg acttcgcagc gggcgagtcg gattgacccg   2520
gtagggattt cgccagatca atgcccgtgg ttttgttcag cttctccagc aagctagcga   2580

tttgggtagc gctgccttcc ccttcgccaa tcacagtgat cgactccacg tcgatatctg   2640
gcacggtgcc tgaaagcgtg acgagcaggg actcgaagct tgcatgcctg caggtcgact   2700
```

```
ctagagcttt atgcttgtaa accgttttgt gaaaaaattt ttaaaataaa aaaggggacc   2760
tctagggtcc ccaattaatt agtaatataa tctattaaag gtcattcaaa aggtcatcca   2820
ccggatcaat tccccctgctc gcgcaggctg ggtgccaagc tctcgggtaa catcaaggcc   2880
cgatccttgg agcccttgcc ctcccgcacg atgatcgtgc cgtgatcgaa atccagatcc   2940
ttgacccgca gttgcaaacc ctcactgatc cgcatgcccg ttccatacag aagctgggcg   3000
aacaaacgat gctcgccttc cagaaaaccg aggatgcgaa ccacttcatc cggggtcagc   3060
accaccggca agcgccgcga cggccgaggt cttccgatct cctgaagcca gggcagatcc   3120
gtgcacagca ccttgccgta gaagaacagc aaggccgcca atgcctgacg atgcgtggag   3180
accgaaacct tgcgctcgtt cgccagccag acagaaatg cctcgacttc gctgctgccc   3240
aaggttgccg ggtgacgcac accgtggaaa cggatgaagg cacgaaccca gtggacataa   3300
gcctgttcgg ttcgtaagct gtaatgcaag tagcgtatgc gctcacgcaa ctggtccaga   3360
accttgaccg aacgcagcgg tggtaacggc gcagtggcgg ttttcatggc ttgttatgac   3420
tgtttttttg gggtacagtc tatgcctcgg gcatccaagc agcaagcgcg ttacgccgtg   3480
ggtcgatgtt tgatgttatg gagcagcaac gatgttacgc agcagggcag tcgccctaaa   3540
acaaagttaa acatcatgag ggaagcggtg atcgccgaag tatcgactca actatcagag   3600
gtagttggcg tcatcgagcg ccatctcgaa ccgacgttgc tggccgtaca tttgtacggc   3660
tccgcagtgg atggcggcct gaagccacac agtgatattg atttgctggt tacggtgacc   3720
gtaaggcttg atgaaacaac gcggcgagct tgatcaacg accttttgga aacttcggct   3780
tcccctggag agagcgagat tctccgcgct gtagaagtca ccattgttgt gcacgacgac   3840
atcattccgt ggcgttatcc agctaagcgc gaactgcaat ttggagaatg gcagcgcaat   3900
gacattcttg caggtatctt cgagccagcc acgatcgaca ttgatctggc tatcttgctg   3960
acaaaagcaa gagaacatag cgttgccttg gtaggtccag cggcggagga actctttgat   4020
ccggttcctg aacaggatct atttgaggcg ctaaatgaaa ccttaacgct atggaactcg   4080
ccgcccgact gggctggcga tgagcgaaat gtagtgctta cgttgtcccg catttggtac   4140
agcgcagtaa ccggcaaaat cgcgccgaag gatgtcgctg ccgactgggc aatggagcgc   4200
ctgccggccc agtatcagcc cgtcatactt gaagctagac aggcttatct tggacaagaa   4260
gaagatcgct tggcctcgcg cgcagatcag ttggaagaat ttgtccacta cgtgaaaggc   4320
gagatcacca aggtagtcgg caaataatgt ctaacaattc gttcaagccg acgccgcttc   4380
gcggcgcggc ttaactcaag cgttagatgc actaagcaca taattgctca cagccaaact   4440
atcaggtcaa gtctgctttt attatttta agcgtgcata ataagcccta cacaaattgg   4500
gagatatatc atgaaaggct ggcttttct tgttatcgca atagttggcg aagtaatcgc   4560
aacatccgca ttaaaatcta gcgagggctt tactaagctg atccggtgga tgaccttttg   4620
aatgaccttt aatagattat attactaatt aattggggac cctagaggtc ccctttttta   4680
ttttaaaaat tttttcacaa aacggtttac aagcataaag ctctagagga tcggcggccg   4740
cggatccccg ggtaccgagc tcgaatttcg agcttctgga gcaggaagat gtcgcgggca   4800
ttagcaccag cggtctgcca agcctccgcc agccgttggg tcccttccgc ttgagctttt   4860
ccatcttcga cgatacgggc ggcggccccc cgcgcttccg cgatcgcccg tttacaagct   4920
gcctcagctg ggcgatcac atcggcttga agttgctgct gcacctgttt gatccgctcc   4980
tgctgcacag ggagttctgc ttggctacga gcgacttcgg tagcaatgtc cgcttcagct   5040
```

```
tcggccacca ccgcttcgcg ccgcgtcaac gcatcctgaa tccggcgctc ggcctcggct    5100
tgggcgatcg ctacatcgcg atcgatccga cgcagggccg tgatcttgtc attttcggcc    5160
gtttggatcg cagaggcagc ctgggcatcg gcttcagcaa ttcgggcatc tcgctgcaga    5220
tcagcccgct gcttgcgtcc actagccgag agataaccga cctcatcgga aatgttctgg    5280
acttgcagcg tatcgaggac tagacccagc tgctcaaggt catcctccgc ctcttccagc    5340
agacttttgg caaaggcaat tttgtcctcg ttgatctgct ccggcgtgag ctggctaaa     5400 acaccacgca agttgccttc gagggtctcc ttggcaattt gctcgatttc cttacggttt    5460
ttgccaagca gccgctcgat cgcgttgtgg atggtcggtt cttccccagc aatcttgata    5520
ttggcaacgc cttcaacagt caggggaatg ccgcccttgg agaaggcatt ggaaacgcgc    5580
aactcaatga tcatgttggt cagatccatg cggagcgctt tttccagcag aggtacccgc    5640
aggctgctgc cgcccttgac caagcgatag ccaactcggc ggccatcact actgcggcga    5700
ctactgccag caaagatcaa aatttcactg ggttggcaga tgtagtagag attgcgcagg    5760
actaagctgc cagccccggc g                                              5781
```

<210> SEQ ID NO 2
<211> LENGTH: 8082
<212> TYPE: DNA
<213> ORGANISM: Artificial Sequence
<220> FEATURE:
<223> OTHER INFORMATION: Neutral Site vector pAM1579

<400> SEQUENCE: 2

```
agcttgtcat ctgccggatg aggcaaaacc ctgcctacgg cgcgattaca tcgtcccagc      60
gcgatcgctc ttactgttga tggctcgtgc ttaaaaacaa tgcaaacttc accgtttcag     120
ctggtgattt tcgactgtga tggtgtgctt gttgatagcg gaacgcatca ctaatcgcgt     180 cttttgcagac atgctcaatg aactgggtct gttggtgact ttggatgaca tgtttgagca     240
gtttgtgggt cattccatgg ctgactgtct caaactaatt gagcgacggt taggcaatcc     300
tccaccccct gactttgttc agcactatca acgccgtacc cgtatcgcgt tagaaacgca     360
tctacaagcc gttcctgggg ttgaagaggc tttggatgct cttgaattgc cctactgtgt     420
tgcgtccagt ggtgatcatc aaaagatgcg aaccacactg agcctgacga agctctggcc     480
acgatttgag ggacgaatct tcagcgtgac tgaagtaccc cgcggcaagc catttcccga     540 tgtcttttg ttggccgccg atcgcttcgg ggttaatcct acggcctgcg ctgtgatcga     600
agacaccccc ttgggagtag cggcaggcgt ggcggcagga atgcaagtgt ttggctacgc     660
gggttccatg cccgcttggc gtctgcaaga agccggtgcc catctcatt  ttgacgatat     720 gcgactgctg cccagtctgc tccaatcgtc gccaaaagat aactccacag cattgcccaa     780
tccctaaccc ctgctcgcgc cgcaactaca cactaaaccg ttcctgcgcg atcgctctta     840
ctgttgatgg ctcgtgctta aaaacaatgc aaccctaacc gtttcagctg gtgattttcg     900
gacgatttgg cttacaggga taactgagag tcaacagcct ctgtccgtca ttgcacaccc     960
atccatgcac tggggacttg actcatgctg aatcacattt ccttgtccca ttgggcgaga    1020
ggggagggga atcttctgga ctcttcacta agcggcgatc gcaggttctt ctacccaagc    1080
agtggcgatc gcttgattgc agtcttcaat gctggcctct gcagccatcg ccgccaccaa    1140
agcatcgtag gcgggacgtt gttgctccag taaagtcttc gcccgtaaca atccccagcg    1200
actgcgtaaa tccgcttcgg caggattgcg atcgagttgc cgccacagtt gtttccactg    1260
ggcgcgatcg tcagctcccc cttccacgtt gccgtagacc agttgctctg ccgctgcacc    1320
```

```
ggccatcaac acctgacacc actgttccag cgatcgctga ctgagttgcc cctgtgcggc    1380
ttcggcttct agcgcagctg cttggaactg cacaccccg cgaccaggtt gtccttggcg     1440
cagcgcttcc cacgctgaga gggtgtagcc cgtcacgggt aaccgatatc gtcgacaggc    1500
ctctagaccc gggctcgagc tagcaagctt ggccggatcc ggccggatcc gggagtttgt    1560
agaaacgcaa aaaggccatc cgtcaggatg gccttctgct taatttgatg cctggcagtt    1620
tatggcgggc gtcctgcccg ccaccctccg ggccgttgct tcgcaacgtt caaatccgct    1680
cccggcggat ttgtcctact caggagagcg ttcaccgaca acaacagat aaaacgaaag     1740 gcccagtctt tcgactgagc ctttcgtttt atttgatgcc tggcagttcc ctactctcgc    1800
atggggagac cccacactac catcggcgct acggcgtttc acttctgagt tcggcatggg    1860
gtcaggtggg accaccgcgc tactgccgcc aggcaaattc tgttttattg agccgttacc    1920
ccacctacta gctaatccca tctgggcaca tccgatggca agaggcccga aggtccccct    1980
ctttggtctt gcgacgttat gcggtattag ctaccgtttc cagtagttat cccctccat    2040 caggcagttt cccagacatt actcacccgt ccgccactcg tcagcaaaga agcaagctta    2100
gatcgacctg cagggggggg ggggaaagcc acgttgtgtc tcaaaatctc tgatgttaca    2160
ttgcacaaga taaaatata tcatcatgaa caataaaact gtctgcttac ataaacagta     2220
atacaagggg tgttatgagc catattcaac gggaaacgtc ttgctcgagg ccgcgattaa    2280
attccaacat ggatgctgat ttatatgggt ataaatgggc tcgcgataat gtcggcaat     2340 caggtgcgac aatctatcga ttgtatggga agcccgatgc gccagagttg tttctgaaac    2400
atggcaaagg tagcgttgcc aatgatgtta cagatgagat ggtcagacta aactggctga    2460
cggaatttat gcctcttccg accatcaagc attttatccg tactcctgat gatgcatggt    2520
tactcaccac tgcgatcccc gggaaaacag cattccaggt attagaagaa tatcctgatt    2580
caggtgaaaa tattgttgat gcgctggcag tgttcctgcg ccggttgcat tcgattcctg    2640
tttgtaattg tccttttaac agcgatcgcg tatttcgtct cgctcaggcg caatcacgaa    2700
tgaataacgg tttggttgat gcgagtgatt ttgatgacga gcgtaatggc tggcctgttg    2760
aacaagtctg gaaagaaatg cataagcttt tgccattctc accggattca gtcgtcactc    2820
atggtgattt ctcacttgat aaccttattt ttgacgaggg gaaattaata ggttgtattg    2880
atgttggacg agtcggaatc gcagaccgat accaggatct tgccatccta tggaactgcc    2940
tcggtgagtt ttctccttca ttacagaaac ggcttttttca aaaatatggt attgataatc    3000
ctgatatgaa taaattgcag tttcatttga tgctcgatga gttttctaa tcagaattgg     3060 ttaattggtt gtaacactgg cagagcatta cgctgacttg acgggacggc ggctttgttg    3120
aataaatcga acttttgctg agttgaagga tcagatcacg catcttcccg acaacgcaga    3180
ccgttccgtg gcaaagcaaa agttcaaaat caccaactgg tccacctaca acaaagctct    3240
catcaaccgt ggctccctca ctttctggct ggatgatggg gcgattcagg cctggtatga    3300
gtcagcaaca ccttcttcac gaggcagacc tcagcgcccc ccccccctg caggtcgatc     3360 tggtaaccc agcgcggttg ctaccaagta gtgaccgct tcgtgatgca aaatccgctg     3420
acgatattcg ggcgatcgct gctgaatgcc atcgagcagt aacgtggcac cccgcccctg    3480
ccaagtcacc gcatccagac tgaacagcac caagaggcta aaacccaatc ccgccggtag    3540
cagcggagaa ctacccagca ttggtcccac caaagctaat gccgtcgtgg taaaaatcgc    3600
gatcgccgtc agactcaagc ccagttcgct catgcttcct catctaggtc acagtcttcg    3660
```

-continued

```
gcgatcgcat cgatctgatg ctgcagcaag cgttttccat accggcgatc gcgccgtcgc    3720
cctttcgctg ccgtggcccg cttacgagct cgtttatcga ccacgatcgc atccaaatcc    3780
gcgatcgctt cccagtccgg caattcagtc tggggcgtcc gtttcattaa tcctgatcag    3840
gcacgaaatt gctgtgcgta gtatcgcgca tagcggccag cctctgccaa cagcgcatcg    3900
tgattgcctg cctcaacaat ctggccgcgc tccatcacca agatgcggct ggcattacga    3960
accgtagcca gacggtgagc aatgataaag accgtccgtc cctgcatcac ccgttctagg    4020
gcctcttgca ccaaggtttc ggactcggaa tcaagcgccg aagtcgcctc atccagaatt    4080
aaaatgcgtg gatcctctac gccggacgca tcgtggccgg catcaccggc gccacaggtg    4140
cggttgctgg cgcctatatc gccgacatca ccgatgggga agatcgggct cgccacttcg    4200
ggctcatgag cgcttgtttc ggcgtgggta tggtggcagg ccccgtggcc ggggactgt     4260 tgggcgccat ctccttgcat gcaccattcc ttgcggcggc ggtgctcaac ggcctcaacc    4320
tactactggg ctgcttccta atgcaggagt cgcataaggg agagcgtcga tcgaccgatg    4380
cccttgagag ccttcaaccc agtcagctcc ttccggtggg cgcggggcat gactatcgtc    4440
gccgcactta tgactgtctt ctttatcatg caactcgtag gacaggtgcc ggcagcgctc    4500
tgggtcattt tcgcgagga ccgctttcgc tggagcgcga cgatgatcgg cctgtcgctt     4560
gcggtattcg gaatcttgca cgccctcgct caagccttcg tcactggtcc cgccaccaaa    4620
cgtttcggcg agaagcaggc cattatcgcc ggcatggcgg ccgacgcgct gggctacgtc    4680
ttgctggcgt tcgcgacgcg aggctggatg gccttcccca ttatgattct tctcgcttcc    4740
ggcggcatcg ggatgcccgc gttgcaggcc atgctgtcca gcaggtaga tgacgaccat     4800 cagggacagc ttcaaggatc gctcgcggct cttaccagcc taacttcgat cactggaccg    4860
ctgatcgtca cggcgattta tgccgcctcg gcgagcacat ggaacgggtt ggcatggatt    4920
gtaggcgccg ccctataccc tgtctgcctc cccgcgttgc gtcgcggtgc atggagccgg    4980
gccacctcga cctgaatgga agccggcggc acctcgctaa cggattcacc actccaagaa    5040
ttggagccaa tcaattcttg cggagaactg tgaatgcgca aaccaaccct tggcagaaca    5100
tatccatcgc gtccgccatc tccagcagcc gcacgcggcg catctcgggc agcgttgggt    5160
cctggccacg ggtgcgcatg atcgtgctcc tgtcgttgag gacccggcta ggctggcggg    5220
gttgccttac tggttagcag aatgaatcac cgatacgcga gcgaacgtga agcgactgct    5280
gctgcaaaac gtctgcgacc tgagcaacaa catgaatggt cttcggtttc cgtgtttcgt    5340
aaagtctgga aacgcggaag tcagcgccct gcaccattat gttccggatc tgcatcgcag    5400
gatgctgctg gctaccctgt ggaacaccta catctgtatt aacgaagcgc tggcattgac    5460
cctgagtgat ttttctctgg tcccgccgca tccataccgc cagttgttta ccctcacaac    5520
gttccagtaa ccgggcatgt tcatcatcag taacccgtat cgtgagcatc ctctctcgtt    5580
tcatcggtat cattacccccc atgaacagaa atccccctta cacggaggca tcagtgacca    5640
aacaggaaaa aaccgccctt aacatggccc gctttatcag aagccagaca ttaacgcttc    5700
tggagaaact caacgagctg gacgcggatg aacaggcaga catctgtgaa tcgcttcacg    5760
accacgctga tgagctttac cgcagctgcc tcgcgcgttt cggtgatgac ggtgaaaacc    5820
tctgacacat gcagctcccg gagacggtca cagcttgtct gtaagcggat gccgggagca    5880
gacaagcccg tcagggcgcg tcagcggggtg ttggcgggtg tcggggcgca gccatgaccc    5940
agtcacgtag cgatagcgga gtgtatactg gcttaactat gcggcatcag agcagattgt    6000
actgagagtg caccatatgc ggtgtgaaat accgcacaga tgcgtaagga gaaaataccg    6060
```

```
catcaggcgc tcttccgctt cctcgctcac tgactcgctg cgctcggtcg ttcggctgcg    6120
gcgagcggta tcagctcact caaaggcggt aatacggtta tccacagaat cagggggataa    6180 cgcaggaaag aacatgtgag caaaaggcca gcaaaaggcc aggaaccgta aaaaggccgc    6240
gttgctggcg ttttttccata ggctccgccc ccctgacgag catcacaaaa atcgacgctc    6300
aagtcagagg tggcgaaacc cgacaggact ataaagatac caggcgtttc ccctggaag    6360 ctccctcgtg cgctctcctg ttccgaccct gccgcttacc ggatacctgt ccgcctttct    6420
cccttcggga agcgtggcgc tttctcatag ctcacgctgt aggtatctca gttcggtgta    6480
ggtcgttcgc tccaagctgg gctgtgtgca cgaaccccc gttcagcccg accgctgcgc    6540
cttatccggt aactatcgtc ttgagtccaa cccggtaaga cacgacttat cgccactggc    6600
agcagccact ggtaacagga ttagcagagc gaggtatgta ggcggtgcta cagagttctt    6660
gaagtggtgg cctaactacg gctacactag aaggacagta tttggtatct gcgctctgct    6720
gaagccagtt accttcggaa aaagagttgg tagctcttga tccggcaaac aaaccaccgc    6780
tggtagcggt ggtttttttg tttgcaagca gcagattacg cgcagaaaaa aaggatctca    6840
agaagatcct ttgatctttt ctacggggtc tgacgctcag tggaacgaaa actcacgtta    6900
agggattttg gtcatgagat tatcaaaaag gatcttcacc tagatccttt taaattaaaa    6960
atgaagtttt aaatcaatct aaagtatata tgagtaaact tggtctgaca gttaccaatg    7020
cttaatcagt gaggcaccta tctcagcgat ctgtctattt cgttcatcca tagttgcctg    7080
actccccgtc gtgtagataa ctacgatacg ggagggctta ccatctggcc ccagtgctgc    7140
aatgataccg cgagacccac gctcaccggc tccagattta tcagcaataa accagccagc    7200
cggaagggcc gagcgcagaa gtggtcctgc aactttatcc gcctccatcc agtctattaa    7260
ttgttgccgg gaagctagag taagtagttc gccagttaat agtttgcgca acgttgttgc    7320
cattgctgca ggcatcgtgg tgtcacgctc gtcgtttggt atggcttcat tcagctccgg    7380
ttcccaacga tcaaggcgag ttacatgatc ccccatgttg tgcaaaaaag cggttagctc    7440
cttcggtcct ccgatcgttg tcagaagtaa gttggccgca gtgttatcac tcatggttat    7500
ggcagcactg cataattctc ttactgtcat gccatccgta agatgctttt ctgtgactgg    7560
tgagtactca accaagtcat tctgagaata gtgtatgcgg cgaccgagtt gctcttgccc    7620
ggcgtcaaca cgggataata ccgcgccaca tagcagaact ttaaaagtgc tcatcattgg    7680
aaaacgttct cggggcgaaa actctcaag gatcttaccg ctgttgagat ccagttcgat    7740
gtaacccact cgtgcaccca actgatcttc agcatctttt actttcacca gcgtttctgg    7800
gtgagcaaaa acaggaaggc aaaatgccgc aaaaaaggga ataagggcga cacggaaatg    7860
ttgaatactc atactcttcc ttttcaata ttattgaagc atttatcagg gttattgtct    7920
catgagcgga tacatatttg aatgtattta gaaaaataaa caaatagggg ttccgcgcac    7980
atttccccga aaagtgccac ctgacgtcta agaaaccatt attatcatga cattaaccta    8040
taaaaatagg cgtatcacga ggccctttcg tcttcaagaa tt                       8082
```

<210> SEQ ID NO 3
<211> LENGTH: 855
<212> TYPE: DNA
<213> ORGANISM: Synechococcus elongatus

<400> SEQUENCE: 3

```
gtgctctcgc aaattgcaat ctgcatttgg gtggaatcga cggcaatttt gcaggattgc      60
```

| | |
|---|---|
| cagcgggcgc tgtcggccga tcgctatcaa ctccaagtct gtgagtctgg cgaaatgctc | 120 |
| ttggagtatg cccaaaccca tcgtgaccaa atcgactgcc tgattttagt ggcagccaat | 180 |
| cccagcttca gggcagttgt tcagcagctc tgctttgagg gagtggtggt accagcgatt | 240 |
| gtcgtaggcg atcgcgacag tgaggatccc gatgaaccag ccaaagaaca gctctatcac | 300 |
| agcgctgaac tgcacctcgg tatccatcag ctcgagcaat gccctacca agttgatgct | 360 |
| gcactggctg aatttctgcg cttagccccg gtcgagacca tggccgacca catcatgctg | 420 |
| atggggccaa ccacgatcc cgagctatcg agccagcagc gggacctcgc tcagcgacta | 480 |
| caagagcgcc taggctatct cggggtctac tacaagcgtg atcccgatcg ctttctgcgc | 540 |
| aacctacccg cctacgaaag ccaaaagctg caccaagcga tgcagactag ctatcgtgaa | 600 |
| atcgttttga gctattttc gccgaatagc aacctcaacc agagcattga caacttcgtc | 660 |
| aacatggctt tctttgccga tgttccagtc accaaagtgg tagaaattca catggagctg | 720 |
| atggacgagt ttgccaagaa gctccgcgta gagggacgtt cagaggacat tttgctggat | 780 |
| tatcggctga ctttaattga tgtaattgca catctttgtg agatgtatcg acggtctatc | 840 |
| ccacgagaaa cctga | 855 |

<210> SEQ ID NO 4
<211> LENGTH: 309
<212> TYPE: DNA
<213> ORGANISM: Synechococcus elongatus

<400> SEQUENCE: 4

| | |
|---|---|
| atgagccctc gtaaaaccta cattctcaag ctctacgtcg ccggcaatac tccaaactca | 60 |
| gtccgtgccc tcaaaacgct caagaacatt ctcgaagttg aatttcaagg tgtttatgct | 120 |
| ctaaaggtga tcgatgttct caaaaatcct cagttggcag aagaggataa atcctagcg | 180 |
| acgccaaccc tcgccaaggt tctaccactg cctgtccgac ggattattgg tgatttatcc | 240 |
| gaccgtgaga agttttgat tggccttgat ttactctacg gcgaacttca agattccgac | 300 |
| gacttctaa | 309 |

<210> SEQ ID NO 5
<211> LENGTH: 1560
<212> TYPE: DNA
<213> ORGANISM: Synechococcus elongatus

<400> SEQUENCE: 5

| | |
|---|---|
| atgacttccg ctgagatgac tagccctaat aataattctg agcaccaagc catcgctaag | 60 |
| atgcgcacga tgattgaagg ctttgatgat attagtcatg gcggtcttcc aatcgggcga | 120 |
| tcgaccctcg ttagtggtac ttcaggaacc ggcaagaccc tttttctat tcaatttctc | 180 |
| tataacggta ttatcgagtt tgatgagcct ggggttttcg ttactttcga agaaaccccg | 240 |
| caagatatca ttaaaaacgc ccgtagtttt ggctgggatt tagccaagct ggtcgatgag | 300 |
| ggcaaactat ttattcttga tgcttcaccc gatccagaag gtcaagaggt tgttggcggc | 360 |
| ttcgatctct ctgctctgat tgagcggatt aattatgcaa ttcaaaagta tcgagcgcgg | 420 |
| cgggtttcaa ttgactcggt cacgtccgtt ttccagcaat atgatgcctc ttctgtggtt | 480 |
| cgccgcgaac tctttcggtt ggtagctcgc ctaaaacaaa ttggggcaac tacggtcatg | 540 |
| accaccgagc gtatcgagga atatggcccg atcgctcgtt acggtgttga ggaatttgtc | 600 |
| tccgataacg tcgtgattct ccgcaacgtt ttggaagggg agcgccgtcg ccgcaccctc | 660 |
| gaaatcctca agctacgtgg caccagccac atgaaagggg aatatccgtt cacgattacg | 720 |

| gatcatggca | tcaatatctt | cccgctcggg | gcaatgcgcc | ttacgcagcg | atcgtcgaac | 780 |
| gtgcgtgttt | catctggtgt | cgtccgactc | gatgaaatgt | gtggtggggg | cttctttaag | 840 |
| gactcaatca | ttctggcaac | tggcgctaca | ggcactggta | aaactctgtt | agttagccgt | 900 |
| ttcgttgaga | atgcttgtgc | taacaaagag | cgggcgattc | tgttcgctta | tgaagagtca | 960 |
| cgagctcagc | tgctccgcaa | tgcctattca | tggggaatgg | actttgagga | gatggagcgc | 1020 |
| caaaacctcc | tcaaaattgt | ttgcgcctat | cctgaatctg | caggtcttga | agaccatttg | 1080 |
| cagattatta | agtcggagat | caatgacttt | aagccagctc | gtattgcaat | cgactccctc | 1140 |
| tctgctttgg | cgcggggcgt | tagcaacaat | gccttccgcc | aatttgtaat | tggtgtcact | 1200 |
| ggctacgcga | acaagaaga | aatcacggga | ctattcacaa | ataccagtga | tcaatttatg | 1260 |
| ggagcgcatt | cgattactga | ctcccatatc | tcaacaatta | cggatacgat | tatcttgctc | 1320 |
| caatacgtcg | agattcgtgg | cgaaatgtcc | cgcgccatta | acgtcttcaa | gatgcgcgga | 1380 |
| tcttggcatg | acaaagcaat | ccgcgaattc | atgatcagcg | acaaagggcc | ggacatcaag | 1440 |
| gattctttcc | ggaactttga | gcggattatt | tcaggttcgc | caacacggat | taccgtcgat | 1500 |
| gagaaaagcg | aactctcgcg | aattgtgcgc | ggcgttcaag | aaaaagggcc | ggagagctag | 1560 |

<210> SEQ ID NO 6
<211> LENGTH: 18
<212> TYPE: DNA
<213> ORGANISM: Artificial Sequence
<220> FEATURE:
<223> OTHER INFORMATION: rnpB primer

<400> SEQUENCE: 6
gaaacatacc gccgatgg                                                 18

<210> SEQ ID NO 7
<211> LENGTH: 19
<212> TYPE: DNA
<213> ORGANISM: Artificial Sequence
<220> FEATURE:
<223> OTHER INFORMATION: rnpB primer

<400> SEQUENCE: 7
gttgctggtg cgctcttac                                                19

<210> SEQ ID NO 8
<211> LENGTH: 21
<212> TYPE: DNA
<213> ORGANISM: Artificial Sequence
<220> FEATURE:
<223> OTHER INFORMATION: kaiA primer

<400> SEQUENCE: 8
tcgcgacagt gaggatcccg a                                             21

<210> SEQ ID NO 9
<211> LENGTH: 20
<212> TYPE: DNA
<213> ORGANISM: Artificial Sequence
<220> FEATURE:
<223> OTHER INFORMATION: kaiA primer

<400> SEQUENCE: 9
gtctcgaccg gggctaagcg                                               20

<210> SEQ ID NO 10

```
<211> LENGTH: 22
<212> TYPE: DNA
<213> ORGANISM: Artificial Sequence
<220> FEATURE:
<223> OTHER INFORMATION: kaiBC primer

<400> SEQUENCE: 10
ggaatatccg ttcacgatta cg                                            22

<210> SEQ ID NO 11
<211> LENGTH: 18
<212> TYPE: DNA
<213> ORGANISM: Artificial Sequence
<220> FEATURE:
<223> OTHER INFORMATION: kaiBC primer

<400> SEQUENCE: 11
gacgatcgct gcgtaagg                                                 18

<210> SEQ ID NO 12
<211> LENGTH: 1560
<212> TYPE: DNA
<213> ORGANISM: Artificial Sequence
<220> FEATURE:
<223> OTHER INFORMATION: KaiC/A422V/H423N vector

<400> SEQUENCE: 12
atgacttccg ctgagatgac tagccctaat aataattctg agcaccaagc catcgctaag     60
atgcgcacga tgattgaagg ctttgatgat attagtcatg gcggtcttcc aatcgggcga    120
tcgaccctcg ttagtggtac ttcaggaacc ggcaagaccc ttttttctat tcaatttctc    180
tataacggta ttatcgagtt tgatgagcct ggggttttcg ttactttcga agaaaccccg    240
caagatatca ttaaaaacgc ccgtagtttt ggctgggatt tagccaagct ggtcgatgag    300
ggcaaactat ttattcttga tgcttcaccc gatccagaag gtcaagaggt tgttggcggc    360
ttcgatctct ctgctctgat tgagcggatt aattatgcaa ttcaaaagta tcgagcgcgg    420
cgggtttcaa ttgactcggt cacgtccgtt ttccagcaat atgatgcctc ttctgtggtt    480
cgccgcgaac tctttcggtt ggtagctcgc taaaacaaa ttggggcaac tacggtcatg     540
accaccgagc gtatcgagga atatggcccg atcgctcgtt acggtgttga ggaatttgtc    600
tccgataacg tcgtgattct ccgcaacgtt ttggaagggg agcgccgtcg ccgcacccte    660 gaaatcctca agctacgtgg caccagccac atgaagggg aatatccgtt cacgattacg      720
gatcatggca tcaatatctt cccgctcggg gcaatgcgcc ttacgcagcg atcgtcgaac    780
gtgcgtgttt catctggtgt cgtccgactc gatgaaatgt gtggtggggg cttctttaag    840
gactcaatca ttctggcaac tggcgctaca ggcactggta aaactctgtt agttagccgt    900
ttcgttgaga atgcttgtgc taacaaagag cgggcgattc tgttcgctta tgaagagtca    960
cgagctcagc tgctccgcaa tgcctattca tggggaatgg actttgagga gatggagcgc   1020
caaaacctcc tcaaaattgt ttgcgcctat cctgaatctg caggtcttga agaccatttg   1080
cagattatta gtcggagat caatgacttt aagccagctc gtattgcaat cgactccctc    1140
tctgctttgg cgcggggcgt tagcaacaat gccttccgcc aatttgtaat tggtgtcact   1200
ggctacgcga acaagaaga atcacgggga ctattcacaa ataccagtga tcaatttatg    1260
ggagtaaatt cgattactga ctcccatatc tcaacaatta cggatacgat tatcttgctc   1320
caatacgtcg agattcgtgg cgaaatgtcc cgcgccatta acgtcttcaa gatgcgcgga   1380
tcttggcatg acaaagcaat ccgcgaattc atgatcagcg acaaagggcc ggacatcaag   1440
```

```
gattctttcc ggaactttga gcggattatt tcaggttcgc caacacggat taccgtcgat        1500
gagaaaagcg aactctcgcg aattgtgcgc ggcgttcaag aaaaagggcc ggagagctag        1560

<210> SEQ ID NO 13
<211> LENGTH: 1560
<212> TYPE: DNA
<213> ORGANISM: Artificial Sequence
<220> FEATURE:
<223> OTHER INFORMATION: KaiC/EE vector

<400> SEQUENCE: 13
atgacttccg ctgagatgac tagccctaat aataattctg agcaccaagc catcgctaag          60
atgcgcacga tgattgaagg cttttgatgat attagtcatg gcggtcttcc aatcgggcga        120
tcgaccctcg ttagtggtac ttcaggaacc ggcaagaccc ttttttctat tcaatttctc        180
tataacggta ttatcgagtt tgatgagcct ggggttttcg ttactttcga agaaaccccg        240
caagatatca ttaaaaacgc ccgtagtttt ggctgggatt tagccaagct ggtcgatgag        300
ggcaaactat ttattcttga tgcttcaccc gatccagaag gtcaagaggt tgttggcggc        360
ttcgatctct ctgctctgat tgagcggatt aattatgcaa ttcaaaagta tcgagcgcgg        420
cgggtttcaa ttgactcggt cacgtccgtt ttccagcaat atgatgcctc ttctgtggtt        480
cgccgcgaac tctttcggtt ggtagctcgc ctaaaacaaa ttggggcaac tacggtcatg        540
accaccgagc gtatcgagga atatggcccg atcgctcgtt acggtgttga ggaatttgtc        600
tccgataacg tcgtgattct ccgcaacgtt ttggaagggg agcgccgtcg ccgcacccctc       660 gaaatcctca agctacgtgg caccagccac atgaaagggg aatatccgtt cacgattacg        720
gatcatggca tcaatatctt cccgctcggg gcaatgcgcc ttacgcagcg atcgtcgaac        780
gtgcgtgttt catctggtgt cgtccgactc gatgaaatgt gtggtggggg cttctttaag        840
gactcaatca ttctggcaac tggcgctaca ggcactggta aaactctgtt agttagccgt        900
ttcgttgaga atgcttgtgc taacaaagag cgggcgattc tgttcgctta tgaagagtca        960
cgagctcagc tgctccgcaa tgcctattca tggggaatgg actttgagga gatggagcgc       1020
caaaacctcc tcaaaattgt ttgcgcctat cctgaatctg caggtcttga agaccatttg       1080
cagattatta gtcggagat caatgacttt aagccagctc gtattgcaat cgactccctc       1140
tctgctttgg cgcgggggcgt tagcaacaat gccttccgcc aatttgtaat tggtgtcact       1200
ggctacgcga acaagaaga atcacgggga ctattcacaa ataccagtga tcaatttatg       1260
ggagcgcatt cgattactga ctcccatatc gaagaaatta cggatacgat tatcttgctc       1320
caatacgtcg agattcgtgg cgaaatgtcc cgcgccatta acgtcttcaa gatgcgcgga       1380
tcttggcatg acaaagcaat ccgcgaattc atgatcagcg acaaagggcc ggacatcaag       1440
gattctttcc ggaactttga gcggattatt tcaggttcgc caacacggat taccgtcgat       1500
gagaaaagcg aactctcgcg aattgtgcgc ggcgttcaag aaaaagggcc ggagagctag       1560

<210> SEQ ID NO 14
<211> LENGTH: 2265
<212> TYPE: DNA
<213> ORGANISM: Synechococcus elongatus

<400> SEQUENCE: 14
atgctggcac catcctcaaa ttgctcccctt gccagccagc ggctgactcc tgaaggttt          60 gctcagttac agagtgcttt gcaagatttt gtggcaacac tgccccaagc gttttattgg        120
```

```
gatagtcgat cgctgcatac gcatctgcgg acccaaacgg gagattgtgc gatcgcgatc      180
gcagcagggt ttcagctgct gttgttaggg cggactgccg cagagtattg ccagcctcac      240
cccttaagcg aacctcacca tgtcagtgtg cagtttggtg ctgacagtat tcagcgctat      300
tgccaagcga cgaatttacc agttgaatac cagcctgcct tggctcaact cggcgacctc      360
agtctcaacc cagacttgat cagtcaattc agtaatcttt tgattgccgc gatcgctgct      420
gatcgagcac cattagcagc tcaatatcct gctgtttccg tctgtcaacc gctagaacaa      480
gctcttcatt ggcaagaaga acaagatcgc ctgatcagtc aagtctctgc acaaattcgt      540
ctcagtttag atctctcaga aattctgaca actacgatcc gtgaaattcg tcagttgctt      600
aatgccgatc gtgcgattat ctatcaattt aagccgcaat gtcttgacgc tggactcgat      660
caacgttggc cactttatat tccaagtcag tcctacatta cctacgaaga tcgtcgcaac      720
gaagcacttt tgtcggtgat cgatcctcta gtccaaccag ggctattaat cacgacagag      780
gaatggcaac ggttccagca aggggaaacg cttctcattg attcagttgg cttctataag      840
gaaagactgc cggagcagta ttccttctat gaacgtgttc aagtgcgatc ggtttgtaaa      900
attccgatcc tagtgcaggg gcgaatttgg ggcttactcg ttgcccatca atgccagcaa      960
gatcatcggt ggcaacctcg ggagcgtgat attctccagc acctagcaga acacctctcg     1020
atcgccattt accaagcaca gctctacggt cagctccaag atcagacaca gacgttagaa     1080
aaccgcgtgc tggaacgtac ccaagagcta attgatgctc ttgccttggc ccaagcggcc     1140
aatgcggcca agggtgagtt tttggccacc atgagtcatg aactcaggac gcctctgacc     1200
tgtgtgattg ggatgtcaag tacgttgctg cgctgggcct ttggcccttt gaccgagcgg     1260
caaagggaat atataaaggc gattcatgac agcggtgaac acctgctgga actgatcaat     1320
gacattcttg atctgtctca aattgaggca ggtaaagcag ccttacaagt gcgtccattc     1380
tccctttcaa gactggcaac ccaaaccctc aatacccctgc aggaaaaagc ccgtttaggc     1440
gagattcagc tcatgctgga tctccagctc aacaaccgtg tggacgtctt ccgagccgat     1500
ccaaagcgat tgcgccaaat tctcattaat cttctcagta acgctgtcaa atttactgaa     1560
ccccaaggaa ctgtttttcct gcgggtttgg cgagaaggcg atcgcgccat cttttcaagtc     1620 agtgatacgg gaattggaat tcctgaaagt gaacaagctc agctgttcca aaagttccaa     1680
cagctcgata cttccattcg ccgccagtac ggtggcacgg gcctagggct ggctctaacc     1740
aagcagctgg ttgaactaca tggcggtcac attcaaattg aatcaaccgt cggtcagggt     1800
agtaccttta cagtctggat ccccgaacaa acgctgatcg aacccgtcga gcctagaccg     1860
tccatcgata atttgcccgc tggccacatt ctcttactgg aagaagagga tgaagcagct     1920
acggtcgtct gtgaaatgtt gacggcggcg ggctttaagg tgatctggct cgtcgatggc     1980
agcacagctc ttgatcaact cgatttactg cagcccattg tgattctgat ggcttggcca     2040
ccgcccgatc agagctgctt acttctgctg cagcacctcc gagaacacca agccgatccc     2100 catccccgt tagtttttgtt cttgggagaa ccacccgtcg atcccttact cacagcccaa     2160
gcctcagcaa ttttgtccaa gcccctagat ccgcagctgc tgttgacgac cttgcagggg     2220
ctctgcccac ccaacctgtc agagggcgat cgcccgagtt cctag                     2265
```